(12) United States Patent
Halbherr et al.

(10) Patent No.: US 12,403,092 B2
(45) Date of Patent: Sep. 2, 2025

(54) LIPOSOMAL DOXORUBICIN FORMULATION, METHOD FOR PRODUCING A LIPOSOMAL DOXORUBICIN FORMULATION AND USE OF A LIPOSOMAL DOXORUBICIN FORMULATION AS A MEDICAMENT

(71) Applicant: InnoMedica Holding AG, Zug (CH)

(72) Inventors: Stéfan Jonathan Halbherr, Bern (CH); Pascal Halbherr, Bern (CH); Christoph Mathieu, Bern (CH); Patrick Buschor, Bern (CH)

(73) Assignee: InnoMedica Holding AG, Zug (CH)

( * ) Notice: Subject to any disclaimer, the term of this patent is extended or adjusted under 35 U.S.C. 154(b) by 795 days.

(21) Appl. No.: 17/620,327

(22) PCT Filed: Jun. 19, 2020

(86) PCT No.: PCT/EP2020/067196
§ 371 (c)(1),
(2) Date: Dec. 17, 2021

(87) PCT Pub. No.: WO2020/254633
PCT Pub. Date: Dec. 24, 2020

(65) Prior Publication Data
US 2022/0265556 A1    Aug. 25, 2022

(30) Foreign Application Priority Data
Jun. 20, 2019 (EP) ..................... 19181524

(51) Int. Cl.
| | |
|---|---|
| *A61K 9/1271* | (2025.01) |
| *A61K 9/00* | (2006.01) |
| *A61K 31/704* | (2006.01) |
| *A61P 35/00* | (2006.01) |

(52) U.S. Cl.
CPC .......... *A61K 9/1271* (2013.01); *A61K 9/0019* (2013.01); *A61K 31/704* (2013.01); *A61P 35/00* (2018.01)

(58) Field of Classification Search
CPC .. A61K 9/1271; A61K 9/0019; A61K 31/704; A61K 9/1277; A61K 9/1278; A61P 35/00
See application file for complete search history.

(56) References Cited

U.S. PATENT DOCUMENTS

| | | | |
|---|---|---|---|
| 9,895,313 | B2 | 2/2018 | Zhu et al. |
| 2008/0206139 | A1 | 8/2008 | Connor et al. |
| 2013/0323178 | A1 | 12/2013 | Yamauchi et al. |
| 2016/0256389 | A1* | 9/2016 | Zhu ..................... A61K 9/1271 |
| 2016/0339014 | A1 | 11/2016 | Hong et al. |

FOREIGN PATENT DOCUMENTS

| | | |
|---|---|---|
| JP | 2007-533737 A | 11/2007 |
| JP | 2013-539402 A | 8/2017 |
| WO | 2013/125237 A1 | 8/2013 |

OTHER PUBLICATIONS

Nag et al. (Surface Engineering of Liposomes for Stealth Behavior, Pharmaceutics, 2013). (Year: 2013).*
Wei et al.(Cardinal Role of Intraliposome Doxorubicin-Sulfate Nanorod Crystal in Doxil Properties and Performance, ACS Omega 2018). (Year: 2018).*
Voluntary Amendment Corresponding to Canadian Application No. 3,143,443 filed May 7, 2024.
Notice of Allowance Corresponding to Canadian Application No. 3, 143,443 mailed May 22, 2024.
Nichols et al., "Catecholamine Uptake and Concentration by Liposomes Maintaining pH Gradients", Biochimica et Biophysica Acta, 455 (1976), 269-271 See Spc., p. 2.
Cramer et al., "NMR studies of pH-induced transport of carboxylic acids across phospholipid vesicle membranes", Science Direct, Biochemical and Biophysical Research Communications, vol. 75, Issue 2, Mar. 21, 1977, pp. 295-301 See Spc., p. 2.
Barenholz, "Doxil—The first FDA-approved nano-drug: Lessons Learned", Journal of Controlled Release, 160 (2012) 117-134 See Spc., pp. 3, 24 & 25.
Gabizon et al., "Prolonged Circulation Time and Enhanced Accumulation in Malignant Exudates of Doxorubicin Encapsulated in Polyethylene-glycol Coated Liposomes", Cancer Research 54, 987-992, Feb. 15, 1994 See Spc., p. 3.
Solomon et al., "Clinical Pharmacology of Liposomal Anthracyclines: Focus on Pegylated Liposomal Doxorubicin", Science Direct, Clinical Lyphoma and Myeloma, vol. 8, Issue 1, Feb. 2008, pp. 21-32 See Spc., p. 3.
Hong et al. "Direct Comparison of Liposomal Doxorubicin with or without Polyethylene Glycol Coating in C-26 tumor-bearing Mice: Is surface Coating with Polyethylene Glycol Beneficial?", Clinical Cancer Research, vol. 5, 3645-3652, Nov. 1999 See Spc., p. 3 See European Search See International Search.
Wei et al., "Cardinal Role of Intraliposome Doxorubicin-Sulfate Nanorod Crystal in Doxil Properties and Performance", ACS Omega, 2018, 3, 2508-2517 See Spc., p. 4.
Ong et al., "Evaluation of Extrusion Technique for Nanosizing Liposomes", Pharmaceutics, 2016, 8, 36 See Spc., p. 12 & 25.
Nakamura et al., "Comparative studies of polyethylene glycol-modified liposomes prepared using different PEG-modification methods", Biochimica et Biphysica Acta, 1818 (2012) 2801-2807 See Spc., p. 23 See European Search See International Search.
Nag et al., "Surface Engineering of Liposomes for Stealth Behavior", Pharmaceutics 2013, vol. 5, 542-569 See Spc., p. 24 See European Search See International Search.

(Continued)

*Primary Examiner* — Robert A Wax
*Assistant Examiner* — John Seungjai Kwon
(74) *Attorney, Agent, or Firm* — Finch & Maloney PLLC

(57) ABSTRACT

The present invention relates to a liposomal doxorubicin formulation, a method for producing a liposomal doxorubicin formulation and a liposomal doxorubicin formulation for use as a medicament, in particular for use in the treatment of cancer, uterine leiomyosarcoma and adnexal skin cancer.

17 Claims, 12 Drawing Sheets

(56) References Cited

OTHER PUBLICATIONS

Figure 1A:
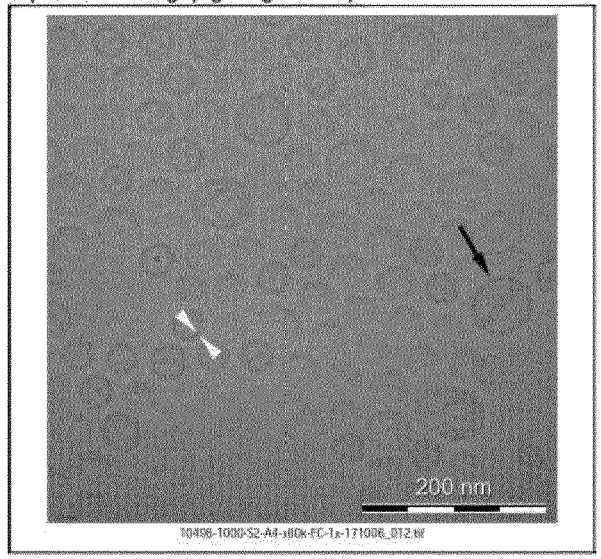

Un et al., "Effects of Liposomal Phospholipids and Lipid Transport-Related Protein on the Intracellular Fate of Encapsulated Doxorubicin", Molecular Pharmaceutics, 2014, vol. 11, 560-567 See European Search See International Search.

European Search Report Corresponding to 19181524.0 mailed Nov. 27, 2019.

International Search Corresponding to PCT/EP2020/067196 mailed Aug. 20, 2020.

Written Opinion Corresponding to PCT/EP2020/067196 mailed Aug. 20, 2020.

P. Patty et al., "The Pressure-Dependence of the Size of Extruded Vesicles", Biophysical Journal, vol. 85, Aug. 2003 pp. 996-1004.

X. Wei et al., "Cardinal Role of Intraliposome Doxorubicin-Sulfate Nanorod Crystal in Doxil Properties and Performance", ACS Omega, 3, Mar. 2, 2018, pp. 2508-2517.

N. Kostevsek et al., "Magneto-Liposomes as MRI Contrast Agents: A Systematic Study of Different Liposomal Formulations", Nanomaterials, 10, 889, May 6, 2020.

Y. Funakoshi, et al., "Effect of Alkyl Chain Length and Unsaturation of the Phospholipid on the Physiochemical Properties of Lipid Nanoparticles", Chemical & Pharmaceutical Bulletin, vol. 63, No. 9, Sep. 2015.

A. Soundararajan et al., "Liposomal doxorubicin (Doxil) in vitro stability, pharmacokinetics, imaging and biodistribution in a head and neck squamous cell carcinoma xenograft model" Nuclear Medicine and Biology, vol. 36, No. 5 Jul. 1, 2009.

G. Navarro et al., "Design of liposomes as carriers for sodium diclofenac", Rev. Colomb. Cienc. Quim. Farm., vol. 27 (2), Dec. 18, 2008, pp. 212-223.

Japanese Decision to Grant Corresponding to 2021-575405 mailed Sep. 10, 2024.

V.A. Coleman et al. "Nanoparticles and metrology: a comparison of methods for the determination of particle size distributions", Proceedings, vol. 8105, Instrumentation, Metrology, and Standards for Nanomanufacturing, Optics, and Semiconductors V; 510504 (2011), https://doi.org/10.1117/12.894297.

A. McLaughlin et al., "Population pharmacokinetics of TLD-1, a novel liposomal doxorubicin, in a phase I trial", Cancer Chemotherapy and Pharmacology, 94, Jun. 15, 2024, pp. 349-360.

I. Colombo et al., "TLD-1, a novel liposomal doxorubicin, in patients with advanced solid tumors: Dose escalation and expansion part of a multicenter open label phase I trial (SAKK 61/16)", European Journal of Cancer, 201, 113588, Feb. 2, 2024.

* cited by examiner

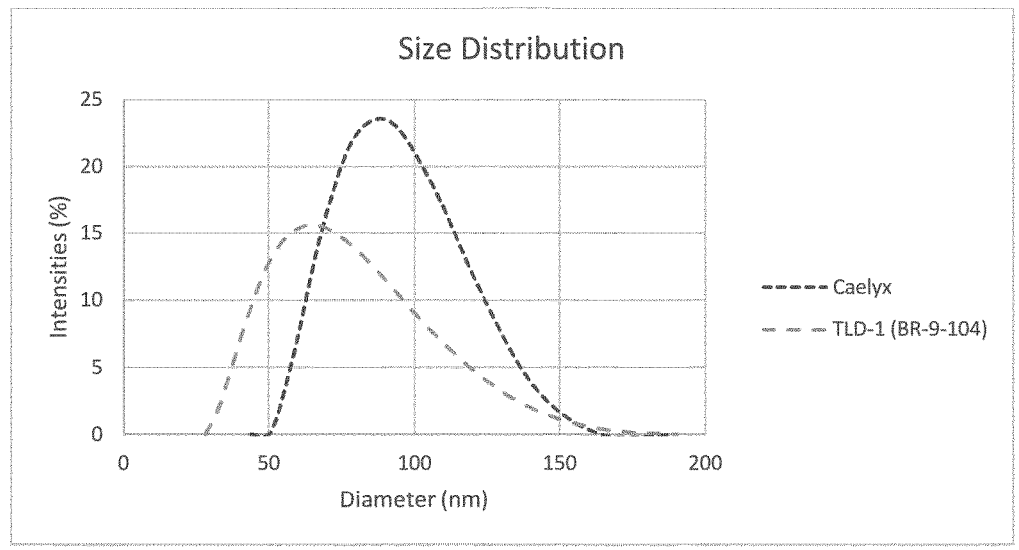
Fig 3
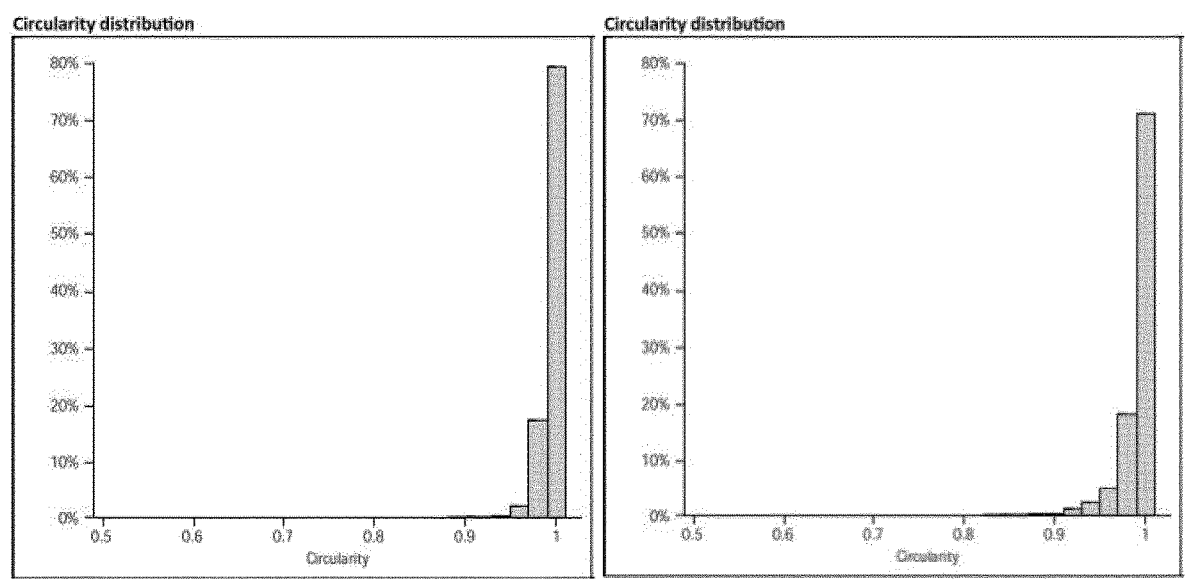
Fig 4a                    Fig 4b

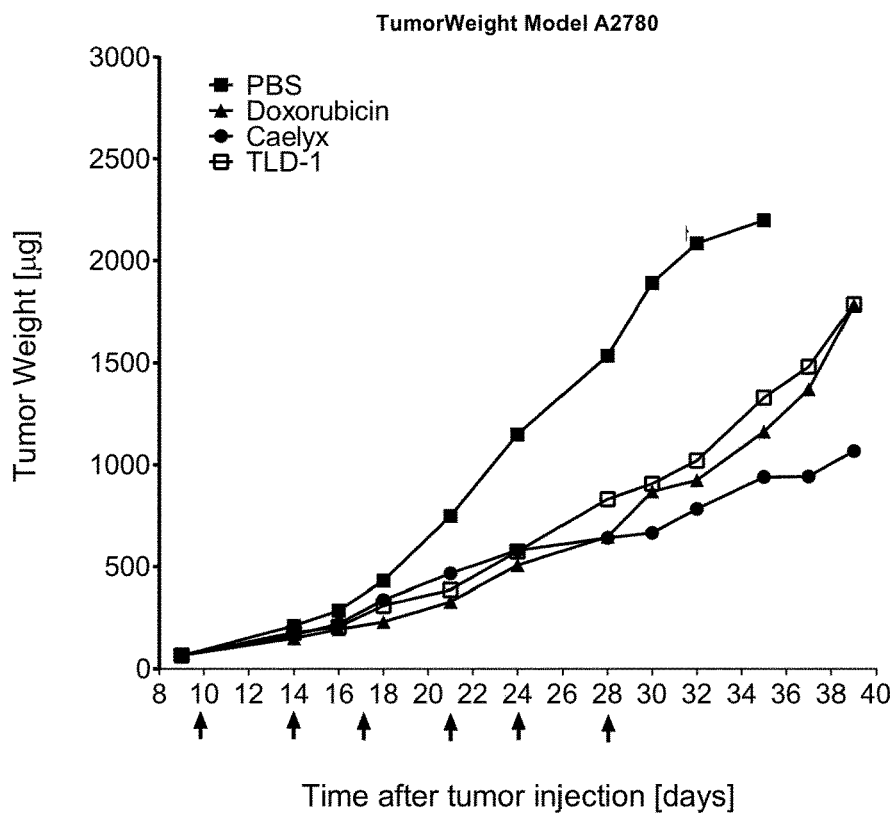
Fig 12a
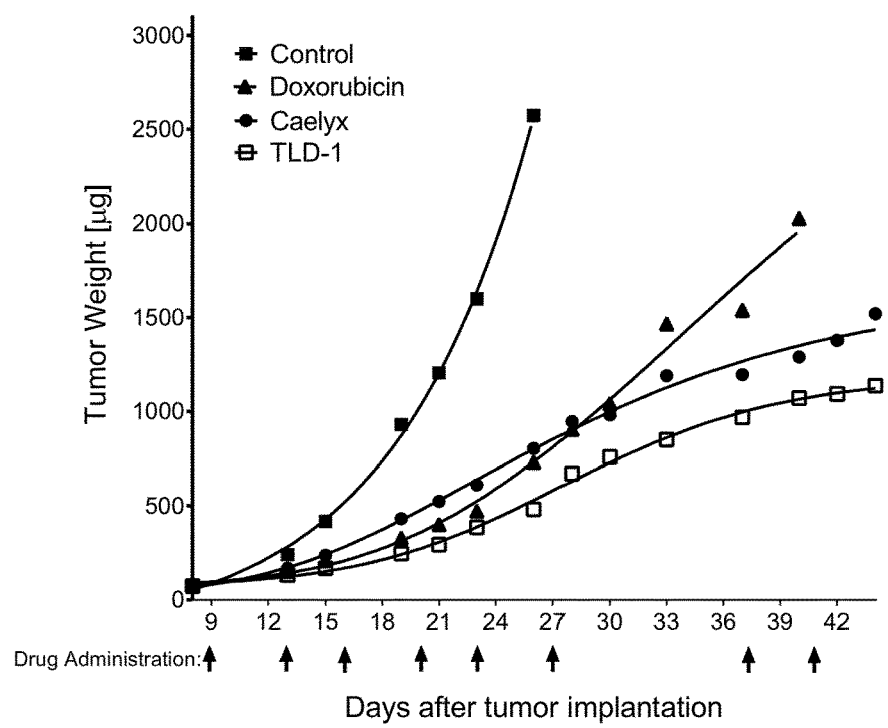
12b

LIPOSOMAL DOXORUBICIN FORMULATION, METHOD FOR PRODUCING A LIPOSOMAL DOXORUBICIN FORMULATION AND USE OF A LIPOSOMAL DOXORUBICIN FORMULATION AS A MEDICAMENT

The present invention relates to a liposomal doxorubicin formulation, a method for producing a liposomal doxorubicin formulation and a liposomal doxorubicin formulation for the use as a medicament.

A liposome is a spherical vesicle having at least one lipid bilayer. Liposomes may also be multivesicular liposomes in which one vesicle contains one or more smaller vesicles. The liposome has an aqueous solution core surrounded by a hydrophobic membrane in the form of a lipid bilayer.

The use of liposomes for drug delivery has been proposed for a variety of drugs, particularly those which are administered parenterally. Liposomes have the potential to provide controlled "depot" release of the administered drug over an extended time period, and to reduce side effects of the drug, by limiting the concentration of free drug in the bloodstream. Liposomes can also alter the tissue distribution and uptake of drugs, in a therapeutically favorable way, and can increase the convenience of therapy, by allowing less frequent drug administration. For example, liposomes may transport encapsulated active components directly to the disease site, including tumour cells and sites of inflammation. The active component can be directly released from the liposome at the treatment site. Thus, a lower dosage of the active component is allowed, and side effects are in consequence limited.

The liposomes may transfer active components to the site of action. Since the liposomal membrane is structurally similar to biological membranes, the liposomes may merge with the cellular membranes. Upon merging, the liposomal contents may be emptied into the cell where the active component can act. The use of liposomes as drug carrier system may reduce the side effects associated with the administration of the respective active component and related to high systematic absorption of the active component. The active component can be accumulated at the desired target. The components of the liposome bilayer may be metabolised in the liver and/or spleen.

The development of drug delivery systems to treat cancer is particularly important as agents in cancer treatment are often cytostatic or cytotoxic. It is desirable to prevent their release to healthy tissue.

Liposomal compositions have been used successfully to deliver entrapped therapeutics. For example, Doxil® (Caelyx® in Europe) is a PEGylated liposomal formulation including entrapped doxorubicin used for treatment of cancer such as ovarian cancer. Weak amphipathic bases like doxorubicin may be loaded into the liposomes using a transmembrane ion gradient. (See, e.g., Nichols et al. (1976) Biochim. Biophys. Acta 455:269-271; Cramer et al (1977) Biochemical and Biophysical Research Communications 75(2):295-301). This loading method, generally referred to as remote loading, typically involves a drug having an ionizable amine group which is loaded by adding it to a suspension of liposomes prepared to have a lower inside/higher outside ion gradient, often a pH gradient.

Once the liposomes have drug loaded PLD (PEGylated Liposomal Doxorubicin) extravasated into interstitial tissues' fluids, little is known of the processes determining drug release. It is believed that gradual loss of the ammonium/proton gradients retaining the drug, enzymatic breakdown of liposomal phospholipids by phospholipases and/or endocytosis by scavenger macrophages likely contribute to drug release. (Barenholz, (2012) J Control Release. 160(2): 117-34).

Liposome-encapsulated doxorubicin has proven effective in the treatment of cancer. However, tumor accumulation, cytotoxicity and efficiency in tumor weight reduction could be further improved.

Liposome-encapsulated doxorubicin has proven less cardio toxic than un-encapsulated doxorubicin. However, liposome-encapsulated doxorubicin as known in the art causes severe side effects, such as palmar-plantar erythrodysesthesia (PPE), more commonly known as hand-foot syndrome. (See, e.g., Gabizon et al (1994) Cancer Research 54:987-992; Solomon et al. (2008) Clinical Lymphoma and melanoma 1:21-32). PPE results in redness, tenderness, and peeling of the skin that can be uncomfortable and even painful. In clinical testing at 50 mg/m dosing every 4 weeks, 50.6% of patients treated with Doxil® developed hand-foot syndrome. The prevalence of this side effect limits the Doxil® dose that can be given as compared with free doxorubicin in the same treatment regimen. Also, liposome-encapsulated doxorubicin as is known in the art continues to cause hematologic side effects, such as neutropenia.

Certain Doxorubicin-loaded liposomes are known from Hong et al. (Clin Cancer Res (1999) 5:3645-3652) and U.S. Pat. No. 9,895,313. However, these liposomes were obtained by different manufacturing processes, namely by a combination of thin-film hydration and extrusion; and by mixing a lipid solution in a water-miscible organic solvent with an aqueous solution in a specially designed multi-port mixing chamber, respectively. Comparative tests carried out according to Hong's instruction for the preparation of liposomes showed that the indicated particle diameters of 65 to 75 nm could not be reproduced. Instead a particle size of about 114 nm was obtained. Moreover, both disclosures remain silent about the circularity of the liposomes, their size distribution or the shape and size of the doxorubicin crystals loaded therein. However, the instructions for the preparation of the studied liposomes indicate an ammonium sulfate concentration of 250 mM, which according to the publication of Wei et al. (Wei et al. (2018) ACS Omega 3:2508-2517) points to liposomes with a pronounced aspect ratio. According to the same publication, a minimum intraliposomal ammonium sulfate concentration of 200 mM is required to support the stable nanocrystallization in pegylated liposomal doxorubicins (PLDs), whereby PLDs lacking such crystals or comprising crystals of poor crystallinity show a quick, biphasic release of doxorubicin.

Therefore, there remains a need for chemically and physically stable liposomal formulations for delivering doxorubicin with improved tumor accumulation, cytotoxicity and efficiency in tumor weight reduction. Also there remains a need to reduce unwanted side effects such as PPE without compromising the therapeutic efficacy. Furthermore, there is a need for an efficient, reliable and cost effective method for producing suitable liposomal formulations.

It is thus an object of the present invention to address those needs and to provide improved liposomal doxorubicin formulations for the treatment of cancer. It is another object of the present invention to provide a method of producing such liposomal doxorubicin formulations and to provide the use of such liposomal doxorubicin as a medicament.

The problem has been solved by a liposomal doxorubicin formulation, a method for producing liposomal doxorubicin formulations and the use of a liposomal doxorubicin formulation as a medicament, having the features according to the independent claims.

The invention relates to a liposomal doxorubicin formulation, wherein the lipid bilayer of the liposomes comprises at least
phosphatidylcholine, preferably 1,2-distearoyl-sn-glycero-3-phosphocholine (DSPC);
cholesterol;
a polyethyleneglycol-lipid conjugate, preferably DSPE-PEG 2000;
wherein
the liposomes have a mean diameter between 30 and 70 nm, preferably between 40 and 65 nm, measured by DLS; or
the liposomes have a mean diameter between 20 and 50 nm, preferably between 30 and 40 nm, measured based on Cryo-TEM acquired images.

By "liposomal doxorubicin formulation" is meant a composition comprising doxorubicin encapsulated in liposomes. In particular, the formulation comprises doxorubicin hydrochloride. Doxorubicin is an anthracycline topoisomerase II inhibitor well known in the art for the treatment of cancer. The chemical name is (8S,10S)-10-[(3-amino-2,3,6-trideoxy-α-L-lyxo-hexopyranosyl)oxy]-8-glycolyl-7,8,9,10-tetrahydro-6,8,11-trihydroxy-1-methoxy-5,12-naphthacenedione hydrochloride. The diseases treatable with the liposomal doxorubicin formulation are types of cancer, including acute leukemias, breast cancer, Hodgkin disease, non-Hodgkin lymphomas, and sarcomas. Particularly preferred, the medicament is for treatment of metastatic breast cancer, advanced ovarian cancer, Kaposi's sarcoma and multiple myeloma.

A major factor which determines stability as well as, location and rate of drug release from the liposome is the liposome lipid membrane composition. Other factors are size and morphology of the liposomes in the composition as well as morphology of doxorubicin crystals encapsulated in the liposome.

For the purposes of this invention, phosphatidylcholine in the lipid bilayer can be any of DDPC, DLPC, DMPC, DPPC, DSPC, DOPC, POPC and DEPC or mixtures thereof. Most preferred is 1,2-distearoyl-sn-glycero-3-phosphocholine (DSPC).

Caelyx®/Doxil® is essentially based on fully hydrogenated soy phosphatiylcholine HSPC. HSPC has the following structural formula:

Formula 1

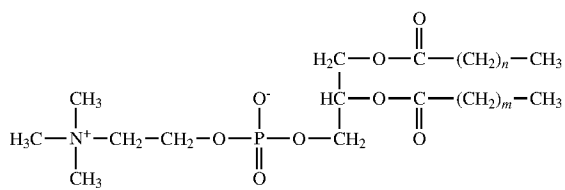

with m,n=14 or 16. Being obtained from a natural product (soyabean), HSPC is structurally less homogeneous than a fully synthetic molecule. HSPC is hence less apt for dense packing of the fatty acid chains when arranged in the lipid bilayer and therefore less suitable to form liposomes of the desired size. The same applies to liposomal formulations, where the amount of phospholipids in the lipid bilayer is formed of mixtures of different phosphatidylcholines, for example of a mixture of 1,2-distearoyl-sn-glycero-3-phosphocholine (DSPC) and 1,2-dipalmitoyl-sn-glycero-3-phosphocholine (DPPC). It is therefore particularly preferred for the purposes of the invention that the total amount of phosphatidylcholine (PC) used for the lipid bilayer comprises at least 95 wt-%, preferably at least 99 wt-% and more preferably 100 wt-% of DSPC.

Liposomes comprising cholesterol in addition to phosphatidylcholine have improved circulation lifetime, pharmacokinetics and therapeutic characteristics. They are biocompatible and biodegradable.

The polyethylenglycol-lipid conjugate is preferably methoxypolyethylene glycol (MPEG), more specifically N-(carbonylmethoxypolyethylene glycol 2000)-1,2-distearoyl-sn-glycero-3-phosphoethanolamine sodium salt, MPEG2000-DSPE). Membrane surface modifications based on polyethylene glycol (PEG)-conjugated lipids are known to improve blood circulation capability, e.g. by avoiding capture of the liposomes by phagocytic cells in the liver and spleen.

The liposomes in the inventive liposomal doxorubicin formulation have a mean diameter between 30 and 70 nm, preferably between 40 and 65 nm, measured by dynamic light scattering DLS and/or the liposomes have a mean diameter between 20 and 50 nm, preferably between 30 and 40 nm, measured by cryo-TEM.

"Measured by dynamic light scattering" (DLS) means that DLS was performed on samples with a lipid concentration between 20 and 30 mg/ml, which were diluted 1/19 in PBS or MQ $H_2O$ to reach an attenuation factor in the instrument of around 6. DLS was measured on a Malvern Zetasizer Nano device at 25° C. and 0° scattering angle. Instrument control and data analysis were performed with the Zetasizer software (version 7.11) from Malvern. Particle size (hydrodynamic diameter) was determined using the Stokes-Einstein equation:

$$d(H) = \frac{kT}{3\pi\eta D} \qquad (Eq. 1)$$

where k is Bolzmann's constant; T is absolute temperature; η is dispersant viscosity and D is diffusion coefficient. Viscosity was determined with the Zetasizer software and was 0.8872 cP. Dispersant refractive index was 1.330. D was obtained by fitting the autocorrelation function with a suitable algorithm. Cumulants analysis is a simple method of analysing the autocorrelation function generated by a DLS experiment and produces the mean particle size (Z-ave) and polydispersity index (PDI). The calculation is defined in ISO 13321 (1996) and ISO 22412 (2008). The first order result from a DLS experiment is an intensity distribution of particle sizes. The intensity distribution is naturally weighted according to the scattering intensity. The size distribution is displayed as a plot of the relative intensity of light scattered by particles (on the Y axis) versus various size classes (on the X axis) which are logarithmically spaced. Clear disposable zeta cells with a pathlength of 10 mm were used for the measurements.

"Measured based on Cryo-TEM acquired images" means that the samples were subject to cryogenic transmission electron microscopy. The liposomal samples diluted as appropriate, vitrified and prepared on-grid (Formvar and Carbon) with an acc. voltage of 200 kV. Images were acquired with a cryoTEM JEOL JEM-2100F a TVIPS TemCam F415MP camera at 20'000×; 40'000×; 80'000× magnification. Particle identification and size determination were performed by semi-automated image processing using Vironova Analyzer Software, Vironova, Sweden. Briefly, a series of random images of the same magnification was imported. Only liposome particles located entirely within the boundaries of the image and with a distinct membrane were detected. The identified objects were analysed for spherical diameter, circularity, unilamellarity. All images were batch-processed with identical thresholds and settings, accumulating over 5 to 18 images for each sample, corresponding 6 to a number of particle analysed of 1560 to 1178. Mean values have a standard deviation of approx. 10 nm.

Usually but not necessarily, the liposomes in the inventive formulation will fall into the numerical ranges of size measured by both methods. The diameter size measured by Cryo-TEM is generally lower than the diameter size measured by DLS. Among other factors, this is due to the PEG-chains being not visible in cryo-TEM images and the hydrodynamic radius having an impact on DLS but not cryo-TEM imaging.

In contrast to the disclosures from the state of the art, it has now surprisingly been found that the liposomal doxorubicin formulations disclosed herein already exhibit stable and particularly uniformly formed doxorubicin crystal fibres at significantly lower intraliposomal ammonium sulfate concentrations.

Without wishing to be bound by theory, it is currently considered that a higher concentration of ammonium sulfate causes more doxorubicin to be loadable, resulting in larger doxorubicin crystals inside the liposome. Owing to their size and rigidity, these doxorubicin crystals expand the interior of the liposome, which ultimately leads to a significant deviation of the liposome from the perfect spherical shape. The different expansion of the particles is also manifested in the occurrence of a major axis and a minor axis, respectively, which can for example be observed in cryogenic transmission electron microscopy (cryo-TEM) images of such pegylated liposomal doxorubicin particles. Of course it also follows that such particles do not feature a high degree of homogeneity, i.e. a narrow particle size distribution and/or a high degree of circularity. However, these properties have a positive effect on the pharmacokinetics and the side effect profile of the liposomal doxorubicin formulations disclosed herein, as will be described in more detail below.

It has successfully been shown that the inventive liposomes of the said composition and the indicated size are more stable than those known in the art. Liposomes of such small diameter are opsonized less rapidly and at a lower extent than their larger counterparts and are cleared less rapidly by the reticuloendothelial system. Also, larger liposomes are more likely to fuse or interact with other liposomes or particles.

As a result, liposomal doxorubicin formulations according to the invention have proven more effective in the prevention of tumor growth. They provide for higher accumulation of doxorubicin in tumors and are more readily accumulated and cleared in the liver. They also have higher cytotoxicity in in vitro assays. Liposomal doxorubicin formulations according to the invention show less pronounced serum leakage compared to Doxil®/Caelyx® formulations, while having good cellular uptake. Serum half-life in humans is considerably higher than the one for the liposomal doxorubicin formulations known in the art. The formulation provides higher drug exposition for a given dose in the relevant target area. Adverse effects such as PPE and neutropenia can significantly be reduced by using the inventive formulation rather than Doxil®/Caelyx®.

The advantages, improved efficacies and reductions in adverse effects will be shown in the examples section hereinafter.

It is preferred that in the liposomal doxorubicin formulation according as describe above, wherein the lipid bilayer essentially consists of synthetic phosphatidylcholine, preferably a structurally uniform type of synthetic phosphatidylcholine, of cholesterol and of DSPE-PEG. It is particularly preferred that the lipid bilayer essentially consists of 1,2-distearoyl-sn-glycero-3-phosphocholine, cholesterol and DSPE-PEG. In particular, at least 95 wt-%, preferably at least 99 wt-%, more preferably 100% of the lipid bilayer consists exclusively of synthetic phosphatidylcholine, preferably a structurally uniform type of synthetic phosphatidylcholine, of cholesterol and of DSPE-PEG. As has been described above, homogeneous lipid bilayer composition is advantageous for dense packing of fatty acid moieties. Homogeneous lipid bilayers hence improve stability of the vesicles.

Preferably, the phosphatidylcholine to cholesterol weight ratio in the lipid bilayer of the liposomes in formulation is from 50:50 to 70:30, preferably from 55:45 to 65:35, more preferably 60:40.

It is preferred that in the liposomal doxorubicin formulation the liposomes have a mean relative circularity of at least 0.99, measured based on Cryo-TEM acquired images, and where the $10^{th}$ percentile is at least 0.98;
preferably where the $5^{th}$ percentile is at least 0.98,
more preferably where the $5^{th}$ percentile is at least 0.98 and the $2^{nd}$ percentile is at least 0.96.

The vesicular morphology of the liposomes is determined as described above (see "measured based on cryo-TEM acquired images"). Circularity is calculated as according to the following formula:

$$\text{Circularity} = \sqrt{\frac{4\pi \times \text{Area}}{\text{Perimeter}^2}}$$

A high mean circularity value of the liposomes in the formulation further supports stability of the vesicles and reduces side effects of the doxorubicin therapy such as PPE and neutropenia. Without being bound to such theory, an ellipsoidal shape together with the size and lipid composition may enable premature release of the drug product in non-targeted locations. Such ellipsoidal shape is characteristic for the approved Caelyx®/Doxil® drug products.

In a preferred embodiment, the liposomal doxorubicin formulation has a polydispersity index ≤0.15, preferably ≤0.10, more preferably ≤0.09, measured by DLS. Such liposomes are therefore essentially monodisperse. Measurement is performed as described above (see "Measured by dynamic light scattering"). A polydispersity index ≤0.15 is superior over the polydispersity indices of liposomal formulations known in the art. Liposomal formulations known in the art, available by extrusion, homogenization, and sonication procedures, typically show polydispersity indices of 0.2 to 0.4 (Gim Ming Ong et al., Evaluation of Extrusion Technique for Nanosizing Liposomes, Pharmaceutics 2016 (8) 36, p. 5). Essentially monodisperse liposomal formulations are beneficial for reproducibility purposes, industrial scale production and compliant with marketing authorization requirements.

Preferably, the liposomes are unilamellar and hold one inner compartment. The liposomes of a liposomal formulation according to the invention are preferably unilamellar to an extent of at least 90%, more preferably to an extent of at least 97%. A homogeneous size, circularity and unilamellarity of the liposomal dispersion provides a controlled and industrially scalable manufacturing process.

In the formulation as described above, the polyethyleneglycol-lipid conjugate, preferably DSPE-PEG, may be located essentially exclusively on the outer layer of the lipid bilayer.

"Essentially exclusively on the outer layer" in the context of the invention refers to an amount of polyethyleneglycol-lipid conjugate, preferably DSPE-PEG, of less than 0.1 mol-%, preferably even less than 0.01 mol-% and more preferably of 0.0 mol-% in the inner layer of the lipid bilayer of the liposomes in the formulation. The essential absence of polyethyleneglycol-lipid conjugate can be ensured by applying a post-modification PEGylation-method as described hereinafter.

PEG-lipids located on the inner surface of liposomes are ineffective, unnecessarily enlarge the size of liposomes, and their hydrolysate may cause an increase in membrane permeability.

It is preferred that the relative amount of polyethyleneglycol-lipid conjugate, preferably DPE-PEG, in the lipid bilayer is at least 2 mol-%, preferably at least 3 mol-%, more preferably between 4 mol-% and 6 mol-%. With the inner layer being essentially free from polyethyleneglycol-lipid conjugate, this results in a relative amount of polyethyleneglycol-lipid conjugate, preferably DSPE-PEG, of up to 12 mol-% on the outer layer of the liposomes in formulation. It is has proven effective to include a high relative amount of polyethyleneglycol-lipid conjugate in the outer surface in order to further improve blood circulation stability and biocompatibility of the vesicles. Surface-modified liposomes were found less likely to be metabolized or scavenged.

It shall be noted that liposomal doxorubicin formulations with a relatively high amount of polyethyleneglycol-lipid conjugate in the lipid bilayer and where the polyethyleneglycol-lipid conjugate, preferably DSPE-PEG, is located essentially exclusively on the outer layer of the lipid bilayer, constitute an advantageous concept of its own, independent of size and morphology of liposomes. This aspect therefore is applicable in combination with the aforementioned description but also on its own.

An aspect of the invention therefore is directed to a liposomal doxorubicin formulation, wherein the lipid bilayer of the liposomes comprises at least
 phosphatidylcholine, preferably 1,2-distearoyl-sn-glycero-3-phosphocholine (DSPC).
 cholesterol;
 a polyethyleneglycol-lipid conjugate, preferably DSPE-PEG 2000;
wherein the relative amount of polyethyleneglycol-lipid conjugate in the lipid bilayer is at least 2 mol-%, preferably at least 3 mol-%, more preferably between 4 mol-% and 6 mol-%, and wherein the polyethyleneglycol-lipid conjugate is located essentially exclusively on the outer layer of the lipid bilayer.

Also preferred are liposomal doxorubicin formulations with a relatively high amount of polyethyleneglycol-lipid conjugate in the lipid bilayer, essentially exclusively on the outer layer of the lipid bilayer, as described in the preceding paragraph, and having, in addition, any other feature or combination of advantageous features as described in this specification, in particular feature(s) regarding size and/or morphology of liposomes.

In a preferred embodiment of the invention, the mean diameter of liposomes in a liposomal doxorubicin formulation according to the invention after 6 months, preferably after 12 months, of storage-time from manufacturing is between 30 and 70 nm, preferably between 40 and 65 nm measured by dynamic light scattering; and/or the mean diameter of the said liposomes is between 20 and 50 nm, preferably between 30 and 40 nm, measured based on cryo-TEM acquired images.

It is particularly preferred that the mean diameter of the liposomes in a formulation after 6 months, preferably after 12 months, from manufacturing is essentially the same as the mean diameter of the liposomes in the formulation immediately after manufacturing. The variation in diameter is not more than ±5 nm, preferably not more than ±2 nm, particularly preferably not more than ±1 nm over a 12-month period from manufacture, measured by DLS. The variation in polydispersity index is not more than ±0.05, preferably not more than ±0.02, particularly preferably not more than ±0.01, measured by DLS.

The liposomes according to the invention are thus particularly stable. The controllability and longevity of the size of liposomes is beneficial for manufacturing, storage, shelf life and patient safety proposes.

The formulation may have a drug to total lipid weight ratio from 0.01 to 0.10, preferably from 0.03 to 0.07. In comparison, the overall lipid content in Doxil® is nearly 16 mg/mL, and 2 mg/mL is the doxorubicin concentration. That results in a drug to lipid ratio of 0.138:1 (wt:wt) for Doxil®. It is an advantage of a lower drug to lipid ratio that the liposomes can be made smaller and more spherical. Such morphology further contributes to the reduced adverse effects. Nevertheless, drug exposition of a patient at a given dose is maintained or even increased as will be shown in the examples section.

It is preferred that the encapsulated doxorubicin crystals have a mean length of 15 to 40 nm, preferably 18 to 37 nm, more preferably 25 to 35 nm, and/or a mean crystal width of 5 to 15 nm, preferably 6 to 12 nm more preferably 7 to 11 nm. The crystal length and width are measured manually from a set of high magnification images obtained by cryo-TEM. The said dimensions are small compared to the similar compositions known in the art. It is further preferred that the encapsulated doxorubicin has a mean number of fibres per liposome of 1 to 6, preferably 2 to 5, more preferably 3 to 4. The number of fibres was determined manually from a set of high magnification images obtained by Cryo-TEM. The number of individual fibers (high density nodes) per crystals could be derived. Note that the doxorubicin crystals have a helical conformation and the number of individual fibers per turn may vary. One measurement was taken per turn of the doxorubicin crystal in order to provide an accurate representation. The said number is small compared to similar compositions known in the art.

It is an advantage of the small dimensions of crystals and of the low number of fibres per crystal that the liposomes can be made smaller and more spherical. Such morphology further contributes to the reduced adverse effects. Nevertheless, drug exposition of a patient at a given dose is maintained or even increased as will be shown in the examples section.

It shall be noted that liposomal doxorubicin formulations with a relatively small fiber width and length of encapsulated doxorubicin crystals in the liposomes, constitute an advantageous concept of its own, independent of size and morphology of liposomes.

An aspect of the invention, which is applicable in combination with the aforementioned description but also on its own, therefore is directed to a liposomal doxorubicin formulation, wherein the lipid bilayer of the liposomes comprises at least phosphatidylcholine, preferably 1,2-distearoyl-sn-glycero-3-phosphocholine (DSPC).
cholesterol;
a polyethyleneglycol-lipid conjugate, preferably DSPE-PEG 2000;

wherein the encapsulated doxorubicin crystals have a mean fibre width of 5 to 15 nm, preferably 6 to 12 nm more preferably 7 to 11 nm, and/or a mean fibre length of 15 to 40 nm, preferably 18 to 37 nm, more preferably 25 to 35 nm.

Also preferred are liposomal doxorubicin formulations with a relatively small fiber width and length, as described in the preceding paragraph, and having, in addition, any other feature or combination of advantageous features as described in this specification, in particular feature(s) regarding size and/or morphology of liposomes.

It is preferred that the formulation is dispersed in HEPES buffered solutions, preferably at a concentration of 10 mM, thereby providing a pH value of 6.8. The solution may contain 0.9% NaCl. Liposomal formulations known in the art are dispersed in buffer solutions based on histidine and sugar groups (myocet lactose, doxil sucrose). In this embodiment, the formulation may be free from sucrose, therefore reducing the risk of bioburden. Also sterile filtration following manufacture is enabled. As will be explained below, this aspect facilitates cost-effective production.

It may be possible to encapsulate active components other than doxorubicin in the formulation. For example, it is possible to comprise or encapsulate active components that show a synergistic effect upon release. At least one active component can also be comprised in the liposomal bilayer and another at least one active component can be encapsulated in the same liposome. The term "active component" may include pharmacologically active drugs as well as pro-drugs. Pro-drugs are medications or compounds that, after administration, are metabolized into pharmacologically active drugs.

The active component can be selected from the group consisting of small or large organic or inorganic molecules, nucleic acids, nucleic acids analogues and derivatives, peptides, peptidomimetics, protein, antibodies and antigen binding fragments thereof, monosaccharides, disaccharides, trisaccharides, oligosaccharides, lipids, glycosaminoglycans, an extract made from biological material, and any combination thereof.

The liposome itself can also be an active component, loaded and unloaded.

According to another aspect of the invention, which is applicable in combination with the aforementioned description but also on its own, it is particularly advantageous to administer liposomal docetaxel formulations together with liposomal doxorubicin formulations. Docetaxel is a chemotherapy medication used in the treatment of cancer, in particular breast cancer, non-small-cell lung cancer, prostate cancer, gastric adenocarcinoma, head and neck cancer. Docetaxel is traded under the name Taxotere, which contains docetaxel as a trihydrate in solvent. The chemical name of docetaxel is [(1S,2S,3R,4S,7R,9S,10S,12R,15S)-4-acetyloxy-1,9,12-trihydroxy-15-[(2R,3S)-2-hydroxy-3-[(2-methylpropan-2-yl)oxycarbonylamino]-3-phenylpropanoyl]oxy-10,14,17,17-tetramethyl-11-oxo-6-oxatetracyclo[11.3.1.03,10.04,7]heptadec-13-en-2-yl]benzoate.

It has been suggested in the art to combine doxorubicin and docetaxel administration for the treatment of certain kinds of cancer. However, it has now been found by the inventors that combined administration of liposomal doxorubicin formulation and liposomal docetaxel formulation has positive effects. Furthermore, it has been found that when administering liposomal formulations where the individual liposomes comprise both drug substances at the same time such effect is even more pronounced. In such an embodiment, the individual liposome encapsulates hydrophilic doxorubicin in its inner aqueous compartment, while docetaxel—having hydrophobic properties—is located in between layers of the lipid bilayer.

It is therefore particularly preferred, if the liposomal doxorubicin formulation comprises individual liposomes which in the aqueous inner compartment comprise doxorubicin; and
in the lipid bilayer comprise docetaxel.

It is particularly preferred that the formulation essentially consists of individual liposomes which in their aqueous inner compartment comprise doxorubicin and in their lipid bilayer comprise docetaxel, i.e. where the amount of liposomes having combined active substances is at least 80%, preferably at least 90%.

It is preferred that the liposomal doxorubicin formulation comprising individual liposomes which in the aqueous inner compartment comprise doxorubicin and in the lipid bilayer comprise docetaxel have the advantageous properties as described herein, i.e. size, circularity, bilayer composition, stability, surface modification etc. It is also preferred that such liposomal doxorubicin formulations are used as a medicament, preferably as a medicament in the treatment of the medical conditions indicated herein. However, it shall be noted that the combination of doxorubicin and docetaxel in individual liposome is an advantageous concept of its own right.

A further aspect of the invention is a method for producing liposomes, preferably liposomes as previously described. Method comprises the steps of:

a) providing phosphatidylcholine, preferably 1,2-distearoyl-sn-glycero-3-phosphocholine (DSPC) and cholesterol in an organic solvent,
b) adding an aqueous liquid,
c) enabling liposome formation by sonication,
d) optionally: separating liposomes by filtration,
e) modifying liposomes by PEGylation,
f) loading doxorubicin into the liposomes, preferably by remote load technique;

characterized in that step c) is carried out such that the liposomes have a mean diameter between 30 and 70 nm, preferably between 40 and 65 nm, measured by dynamic light scattering; and/or
the liposomes have a mean diameter between 20 and 50 nm, preferably between 30 and 40 nm, measured by cryo-TEM.

By means of this method, liposomes with greatly improved stability values, greatly improved bioavailability and reduced toxicity can be obtained. The empty liposomes are manufactured in a gentle sonication process, at which the lipids naturally turn into liposomes. The liposomes remain stable even without the addition of stabilizers in their natural shape over a long period of time. Size distribution of the liposomes has been measured over various points in time and essentially remains constant. The small size also proves constant over time.

Preferably, the organic solvent used in step a) is chosen from the group, consisting of: ethanol, methanol, chloroform and mixtures thereof. Most preferably, organic solvents with high degree of purity are used, e.g. ethanol or methanol absolute >99.99%. Even more preferably, no thin-film hydration is needed.

The used lipids show a good solubility in these organic solvents. By using organic solvents with a high degree of purity contamination of the liposomes with impurities is avoided.

The aqueous liquid used in step b) may be chosen from the group, consisting of: water, aqueous buffer solution, aqueous glycine-solution. Preferably, aqueous buffer solutions with a physiological salt concentration, e.g. PBS (10 mM phosphate, pH 7.2-7.4, 0.9% NaCl) can be used. It is also possible to use the following aqueous buffer solutions: 150 mM ammonium sulphate, 150 nm calcium acetate, 150 mM magnesium acetate, 150 mM manganese acetate, 150 mM iron chloride, or 150 mM copper sulphate.

It is preferred to use aqueous ammonium sulfate solution, preferably 140 to 160 mM aqueous ammonium sulfate solution, more preferably 150 mM aqueous ammonium sulfate solution. Concentrations in the indicated numerical ranges allow controlled remote load in step f) and are suitable to deliver a liposomal doxorubicin formulation with a drug to total lipid weight ratio is from 0.01 to 0.1, preferably from 0.04 to 0.6. A physiological salt concentration can be provided such that the interior of the liposome resembles the physiological conditions in the body.

The sonication in step c) is preferably performed with an amplitude of at least 60 μm and for at least 1 hour. The sonication can be performed up to 24 hours.

The separation step d), if any, can be achieved by centrifugation; filtration; field flow fractionation (FFF); dialysis; chromatographic methods, preferably gel-permeations-chromatography.

The liposomes are separated from remaining substances of the liquid mixture, such as organic solvent, salts and/or detergents.

The liposome distribution is preferably at least 95% unilamellar and preferably at least 97% unilamellar, more preferably at least 98% unilamellar. Preferably, the liposomes have a mean relative circularity of at least 0.99, measured by cryo-TEM, where the 10th percentile is at least 0.98; preferably where the 5th percentile is at least 0.98. Even more preferably where the 5th percentile is at least 0.98 and the 2nd percentile is at least 0.96. Both unilamellarity and circularity are measured as described above. In liposomal formulations according to the invention, the ratio of spherical liposomes to broken particles and/or aggregates in weight-% is higher than 9:1, measured by cryo-transmission electron microscopy.

In step e) the liposomal dispersion is modified by PEGylation.

By "PEGylation" is meant polyethylene glycol-modification which is performed as a post-modification method. Traditionally, phosphatidylcholine, cholesterol and PEG-lipid are dissolved in the same mixture to yield crude liposomes which are downsized later on by extrusion. This method is called the pre-modification method. In contrast, when applying the post-modification method, bare liposomes composed of phosphatidylcholine and cholesterol are prepared in solvent and are then extruded through suitable membrane(s). In a variant of the post-modification method, PEG-derivatized phospholipids are added to a dilute suspension of pre-formed liposomes at temperatures close to the melting temperature of the liposome components. This technique is also referred to as "post-insertion", wherein the insertion of the PEG-derivatized phospholipids is mainly driven by the hydrophobic interaction of the membrane lipids and the hydrophobic part of the PEG-derivatized phospholipids. It is preferred that the PEGylation is performed at 60° to 70° C., preferably at 65° C. The method is described in detail in Nakamura, K.; Comparative studies of polyethylene glycol-modified liposomes prepared using different PEG-modification methods; Biochim Biophys Acta, 1818 (2012) 2801-2807. It is preferred the DSPE-MPEG2000 is used. In another variant of the post-modification method, PEG-modification of liposome surfaces is achieved by covalent attachment of PEG moieties containing a reactive group that can react with a complementary reactive group present on the liposome constituents. A variety of different methods for coupling moieties such as PEG to the surface of preformed liposomes are known, including crosslinking of primary amines by glutaraldehyde, carbonyl-amine bond formation, amide bond formation by the reaction of activated esters with primary amine, disulfide bond formation, thioester bond formation by the maleimide-thiol addition reaction, and hydrazine bond formation. In addition, a variety of biorthogonal approaches such as those usually summarized under the term "click" chemistry exist which allow for chemoselectivity, mild reaction conditions in aqueous media, and good yields with little or no by-products. Examples of click chemistry reactions that have been exploited to modify the surface of liposomes include copper(I)-catalyzed Huisgen 1,3-dipolar cycloaddition (CuAAC), ring-strain promoted copper-free click reaction, Staudinger ligation, and tetrazine/trans-cyclooctene inverse electron demand Diels-Alder cycloaddition (IEDDA), as described in detail in Nag, O. K.; Surface Engineering of Liposomes for Stealth Behavior; Pharmaceutics; 5 (2013) 542-569. In both variants, only after the steps of liposome formation/minimization is a PEG-lipid added, preferably in aqueous solution. Hence, PEGylated liposomes are yielded wherein the DSPE-PEG is located essentially exclusively on the outer layer of the lipid bilayer.

The method has the advantage that small homogeneous liposomes with a mean diameter of less than 50 nm and a higher degree of circularity are yielded which have a higher tendency to be stable. A further relevant aspect of the present invention is reduced manufacturing costs reduced amount of manufacturing steps which facilitates large-scale production.

In step f) doxorubicin is loaded into the liposomes by remote load technique.

By "remote load" is meant an approach for loading doxorubicin into the intraliposomal aqueous phase. Remote load is applied to liposomes already formed. In such liposomal formulations, a transmembrane gradient of ammonium sulphate is established where the $[(NH_4)_2SO_4]$concentration in the aqueous inner of the liposome largely exceeds the $[(NH_4)_2SO_4]$concentration in the outer medium. The gradient serves as a driving force for transferring amphipathic weak base drugs, such as doxorubicin, across the liposome bilayer, where they form a crystalline-like precipitate. The approach was first developed by Barenholz and is well known in the art (see Barenholz, Y. C.; Doxil®—The first FDA-approved nano-drug: Lessons learned; J. Control. Release 2012, 160, 117-134).

It is preferred that the method does not contain any extrusion step and does not contain any thin film hydration step.

By "extrusion" is meant a conventional technique for the preparation of liposomes, where a liposomal formulation is passed through a membrane of defined pore size. Extrusion processes have been discussed in the art as being the method of choice for liposome production (Gim Ming Ong et al., Evaluation of Extrusion Technique for Nanosizing Liposomes, Pharmaceutics 2016 (8) 36; Perrie et al., Manufacturing Methods for Liposome Adjuvants, in; Vaccine Adjuvants: Methods and Protocols, Methods in Molecular Biology, vol. 1494, 2017). Extrusion steps are, however, costly and deliver inferior vesicle morphology values leading to lower quality liposomes.

By "thin-film hydration" is meant a conventional method for the preparation of liposomes, involving the step of making a thin lipid film, e.g. in a round-bottom flask, by removal of organic solvent. Heterogeneous liposomes are then formed upon the addition and agitation of a dispersion medium. Thin film hydration is typically followed by extrusion through polycarbonate membranes in order to obtain more homogeneous formulations of smaller liposomes. Thin-film hydration is even more costly than extrusion.

It has been found that liposomal formulations produced by sonication according to this invention are less polydisperse, more stable and less prone to degradation than liposomes obtainable by conventional techniques. Also, the liposomes have reduced diameters and a higher degree of circularity when compared to those resulting from extrusion processes.

It is preferred that the steps of the method as described above is followed by one more step g). Step g) comprises sterilisation by filtration.

By "sterilisation by filtration" is meant that the finalized liposomal formulation is passed through a sterile filter having a pore size of 0.22 μm in order to retain potential impurities and bacterial organisms.

Sterilisation by filtration allows GMP-compliant manufacturing of the liposomal doxorubicin formulation where the steps prior to sterile filtration do not necessarily need to be performed under sterile conditions. This is particularly cost effective. In order to allow sterilisation by filtration, it is however a prerequisite that the formulation be dispersed in storage buffer solution which is free from sugar groups, such as dispersion in HEPES buffered solution.

The liposomal doxorubicin formulation as previously described may be used as a medicament, in particular for use in the treatment of cancer, more particular for use in the treatment of solid tumors, metastatic breast cancer, advanced ovarian cancer, Kaposi's sarcoma and multiple myeloma.

The liposomal doxorubicin formulation as previously described may be used in particular in the treatment of uterine leiomyosarcoma.

The liposomal doxorubicin formulation as previously described may be used in particular in the treatment of adnexal skin cancer.

The liposomal doxorubicin formulation in the treatment of cancer may be administered intravenously.

For intravenous injection, the liposomes may be present in solved or suspended form. The amount of formulation may be in the range of 1 to 100 ml per m² (body surface) and is dose dependent. The injectable solution can comprise further ingredients, such as stabilising agents. It can also comprise physiologically compatible ingredients such as salt, in particular sodium chloride or alcohol, preferably ethanol.

A further aspect of the invention is liposomes as previously described obtainable by a method as previously described.

The invention will be further explained by the following examples. The examples are not intended to limit the scope of the invention in any way.

Figure 2A:
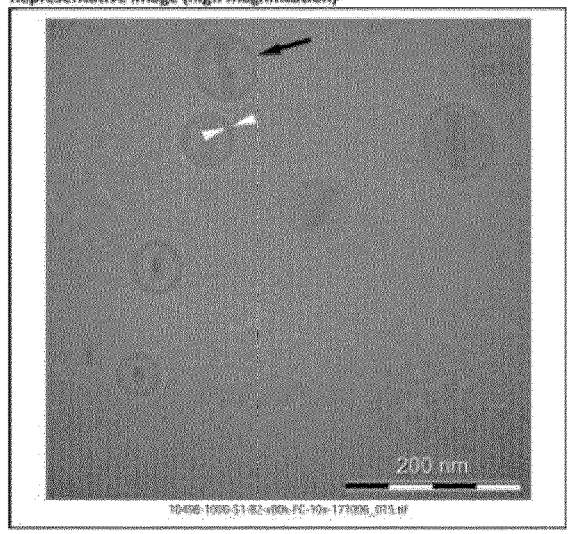
Figure 5A:
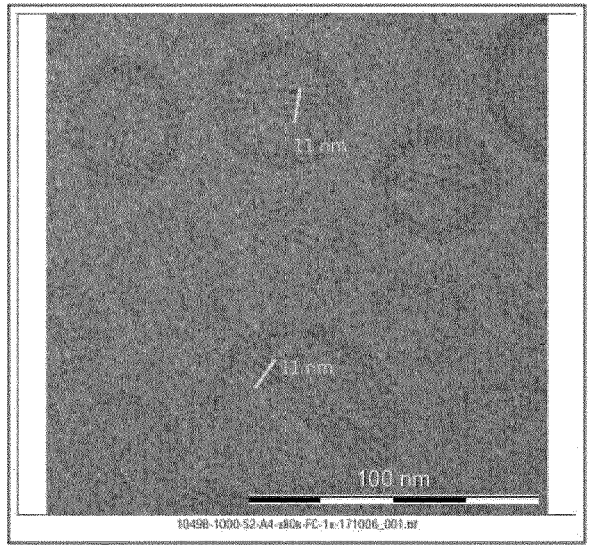
Figure 5B:
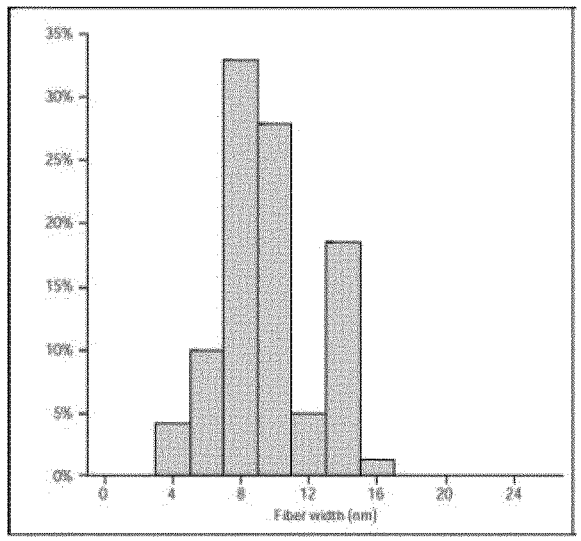
Figure 5C:
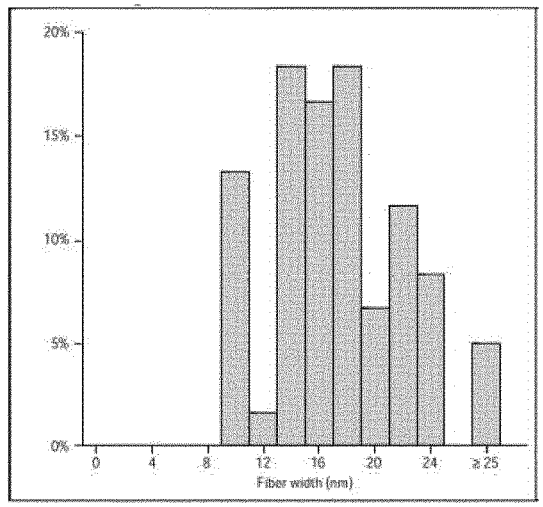
Figure 6A:
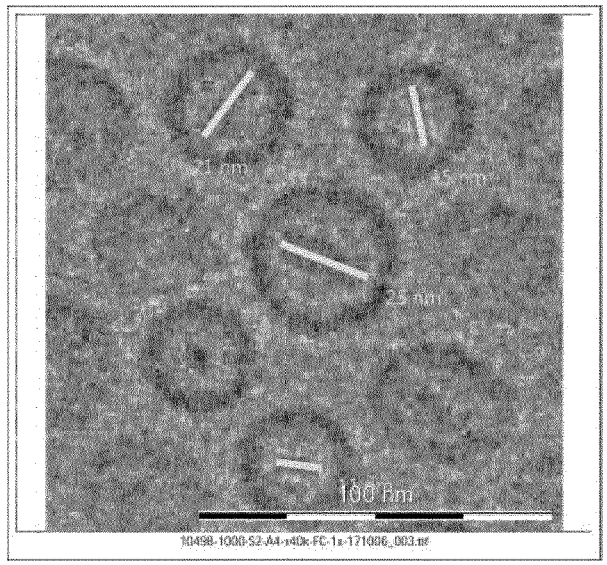
Figure 6B:
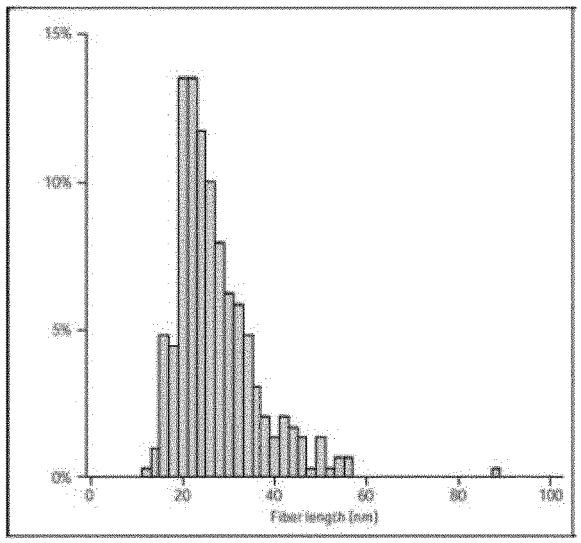
Figure 6C:
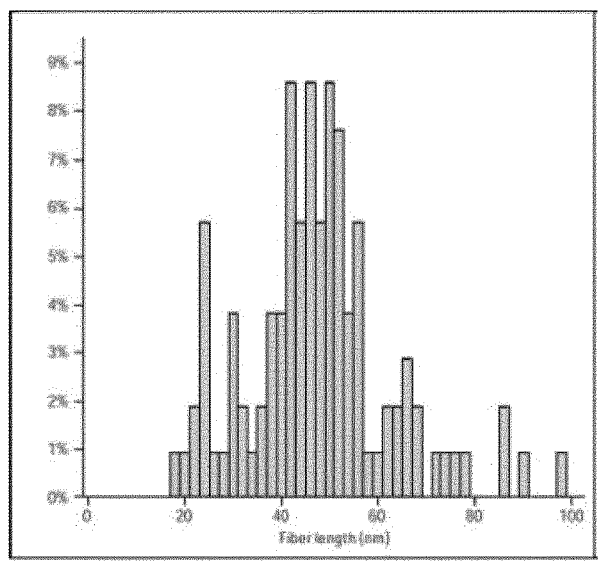
Figure 7A:
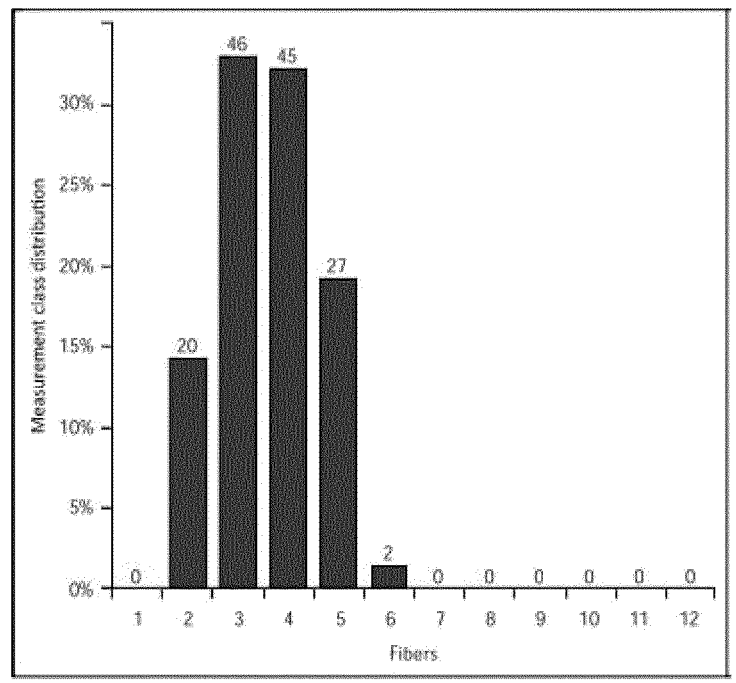
Figure 7B:
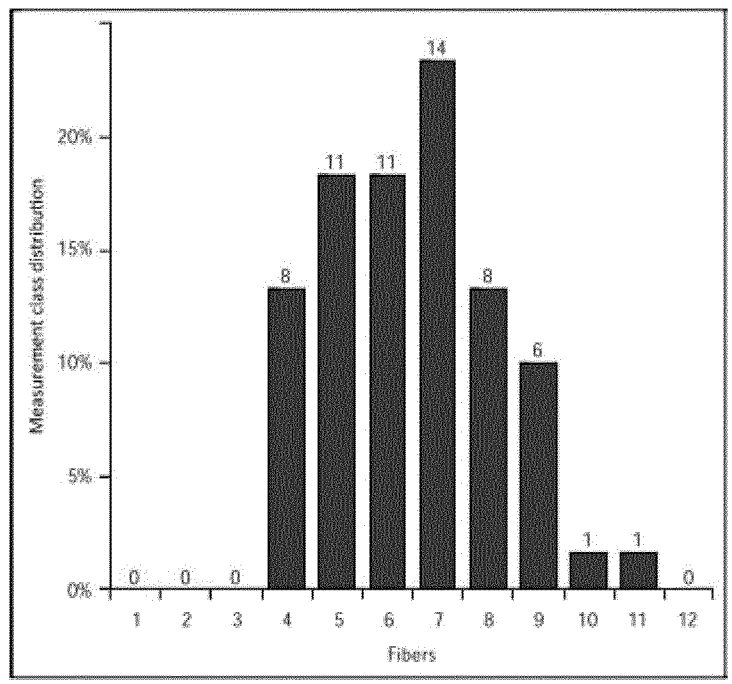
Figure 8A:
Figure 8B:
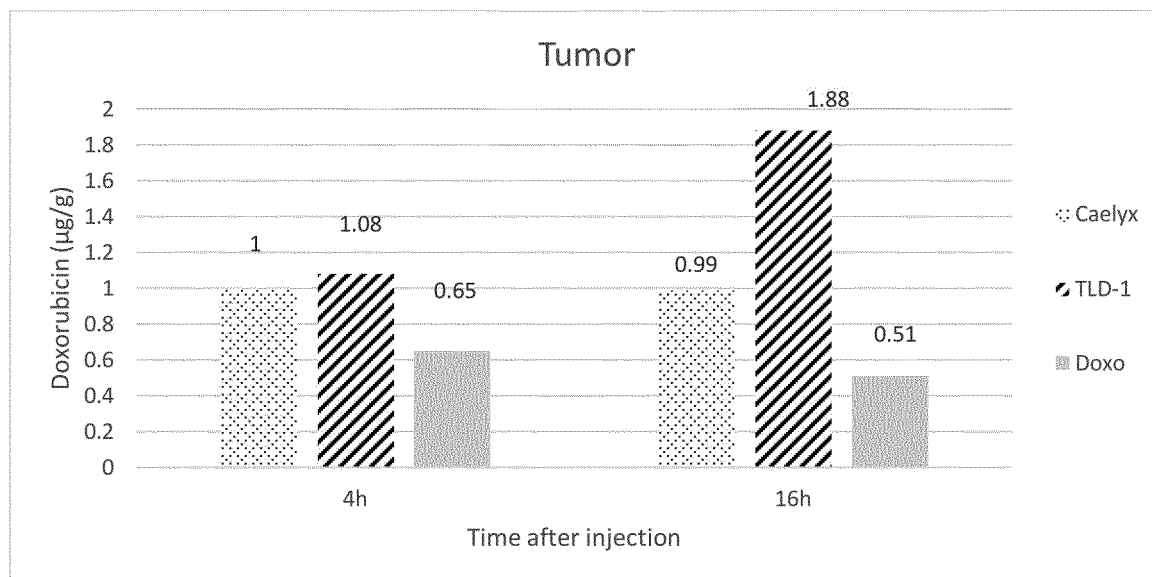
Figure 9:
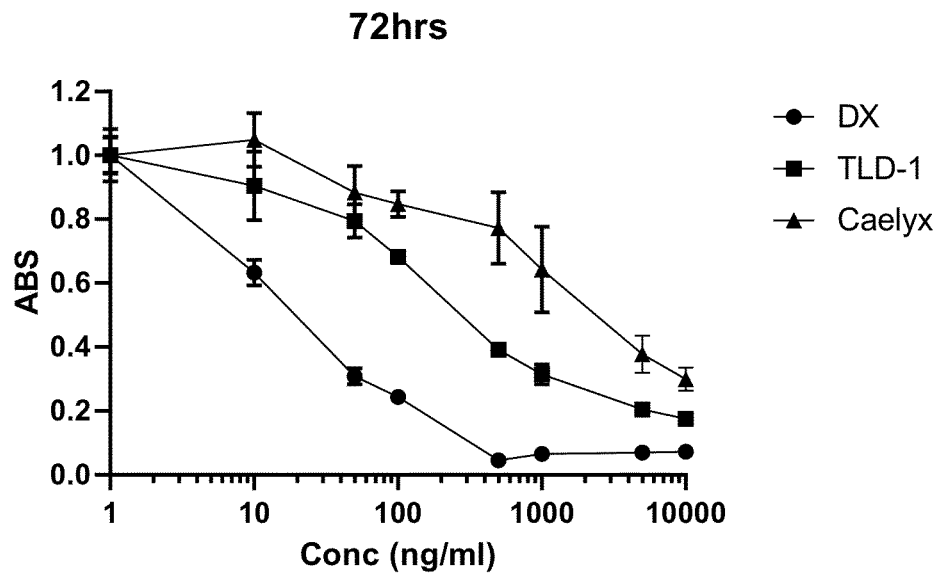
Figure 10A:
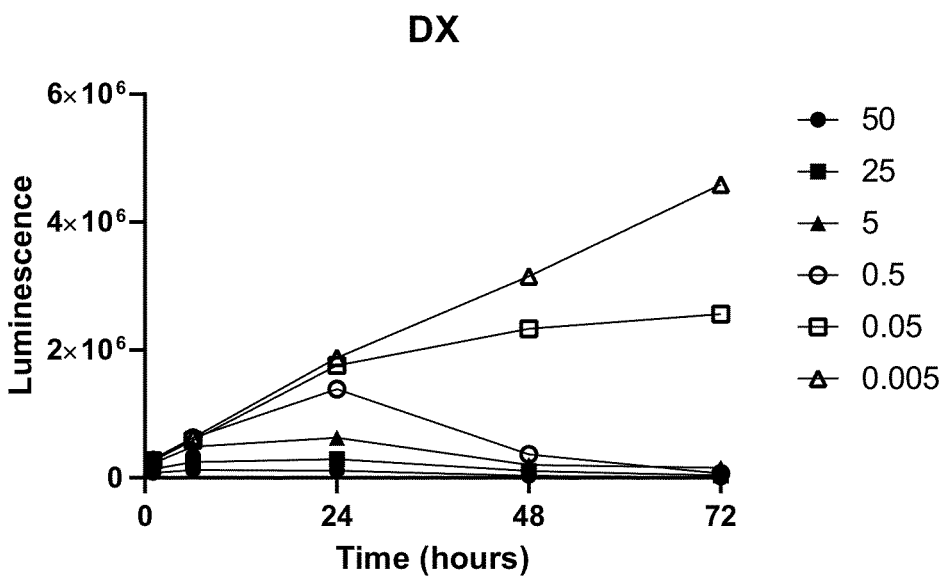
Figure 10B:
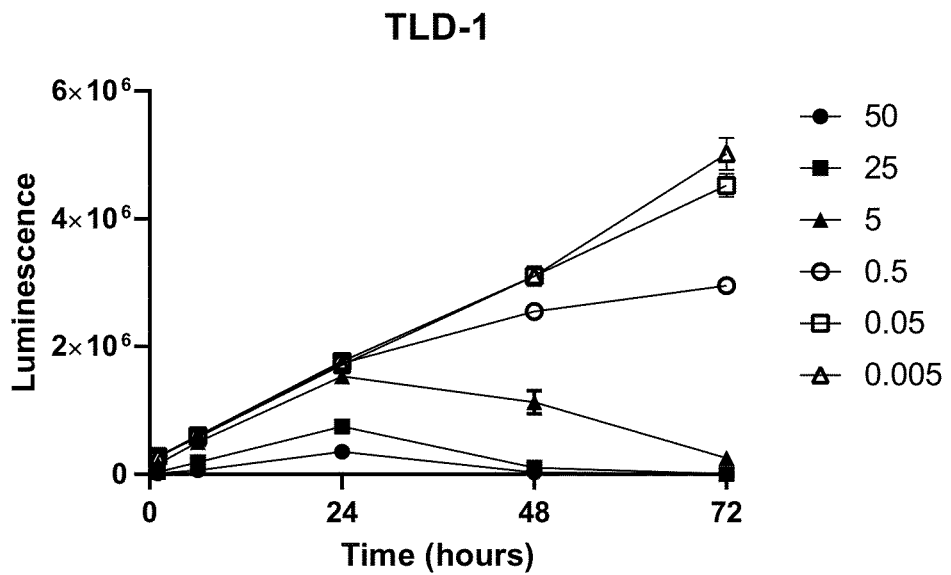
Figure 10C:
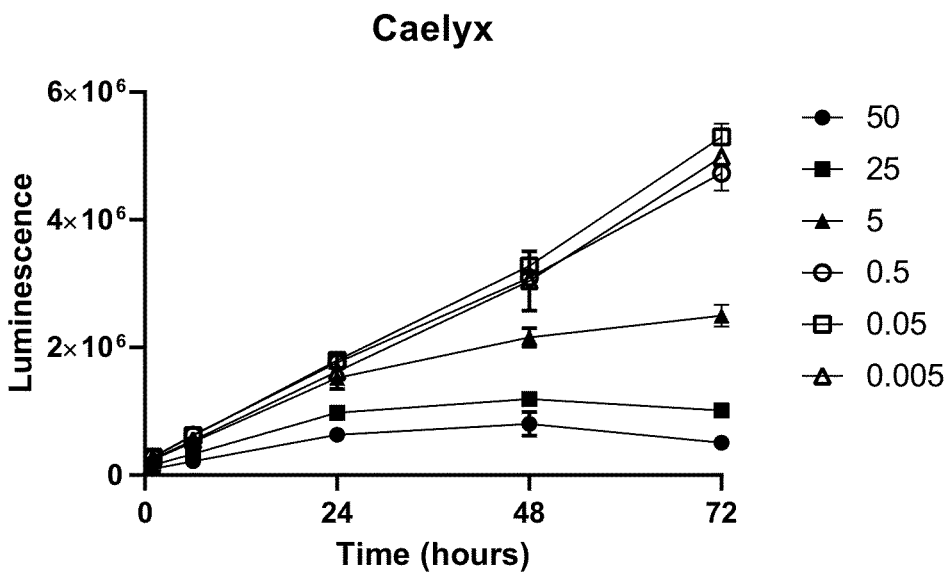
Figure 11:
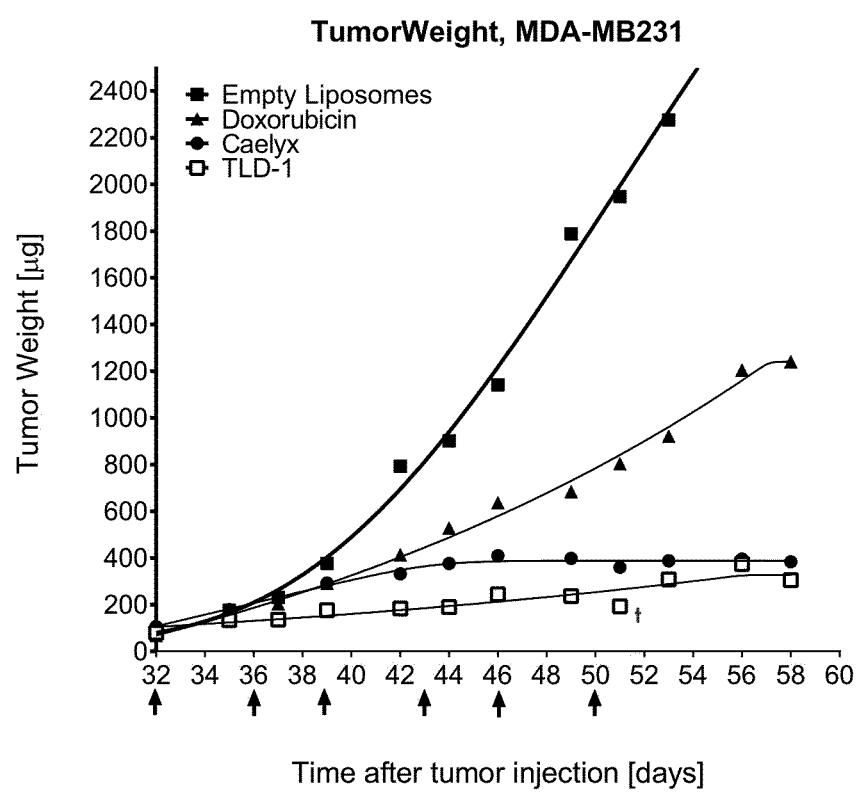
Figure 13:
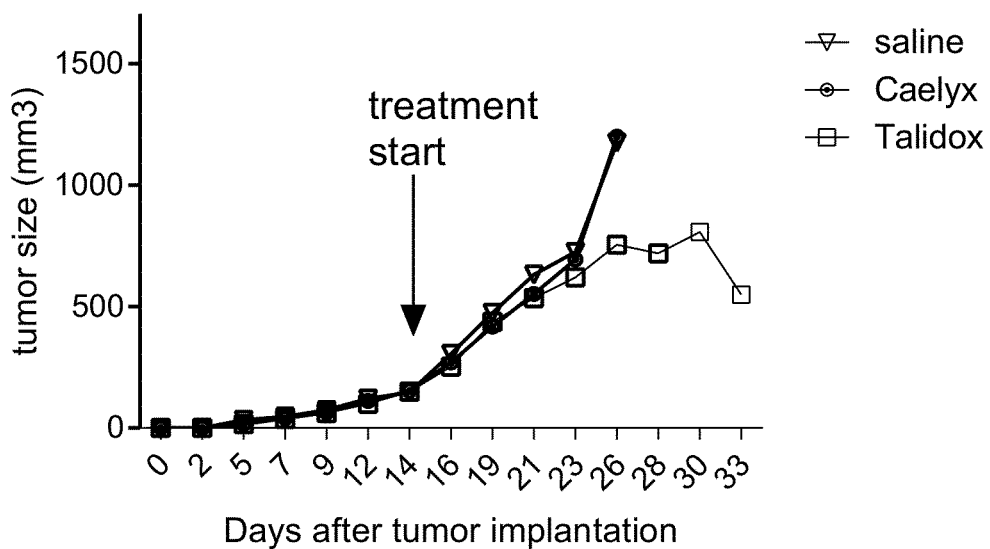
Figure 14:
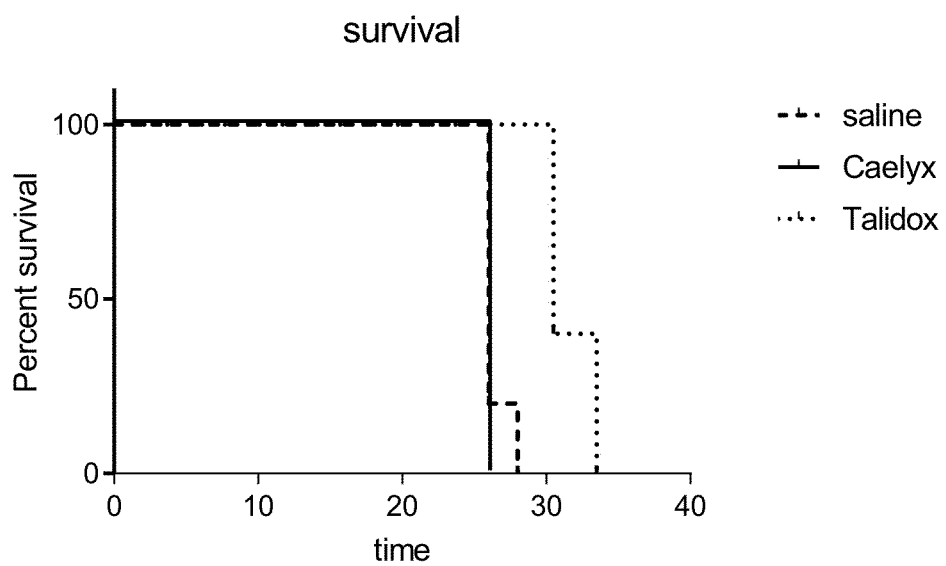

FIG. 1a/1b: morphology and size distribution of liposomal doxorubicin formulation according to the invention measured by cryo-TEM;

FIG. 2a/2b: morphology and size distribution of Caelyx® formulation measured by cryo-TEM;

FIG. 3: size distribution of different embodiments of the liposomal doxorubicin formulation according to the invention compared to Caelyx® formulation measured by DLS;

FIG. 4a-4b: circularity distribution of the liposomal doxorubicin formulation according to the invention (4a) compared to Caelyx® formulation (4b) measured by cryo-TEM;

FIG. 5a-5c: width measurements of the doxorubicin crystals according to the invention (5a, 5b) compared to Caelyx® formulation (5c) measured by cryo-TEM;

FIG. 6a-6c: length measurements of the doxorubicin crystals according to the invention (6a, 6b) compared to Caelyx® formulation (5c) measured by cryo-TEM;

FIG. 7a-7b: count of doxorubicin fibres per liposome, arranged by classes; FIG. 7a represents a doxorubicin formulation according to the invention; FIG. 7b a Caelyx® formulation, measured based on cryo-TEM imaging;

FIG. 8: doxorubicin accumulation in liver and tumor over time for three compared administered formulations CALYX, TLD-1, free DXR;

FIG. 9: in vitro cytotoxicity study of three compared doxorubicin formulations CALYX, TLD-1, free DXR based on MTS absorption;

FIG. 10a-10c: in vitro cytotoxicity study of three compared doxorubicin formulations CALYX, TLD-1, free DXR based on luciferase luminescence;

FIG. 11 results of comparative study on tumor growth (MDAMB231) over time under administration of liposomal doxorubicin formulation according to Expl 1;

FIG. 12a-b: results of comparative study on tumor growth (A2780) over time under administration of liposomal doxorubicin formulation according to Expl 1;

FIG. 13: results of comparative study on tumor growth (4T1) over time under administration of liposomal doxorubicin formulation according to Expl 1;

FIG. 14: results of in-vivo survival study in mice for three compared doxorubicin formulations including the one according to Expl 1.

Figure 15A:
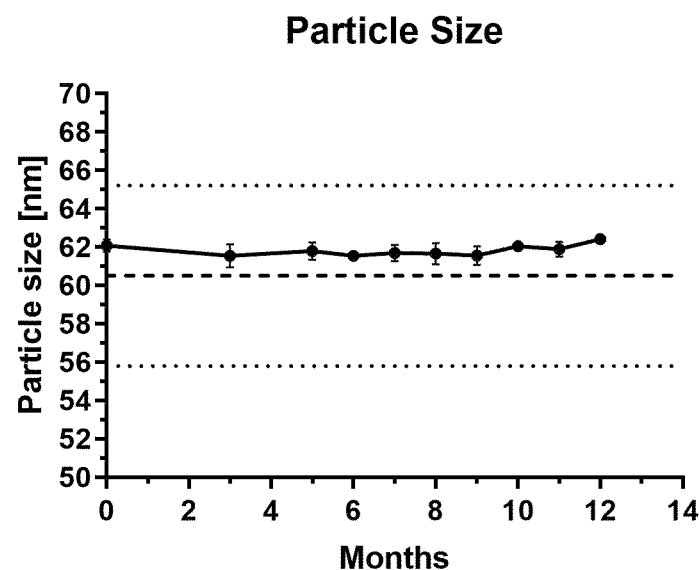
Figure 15B:
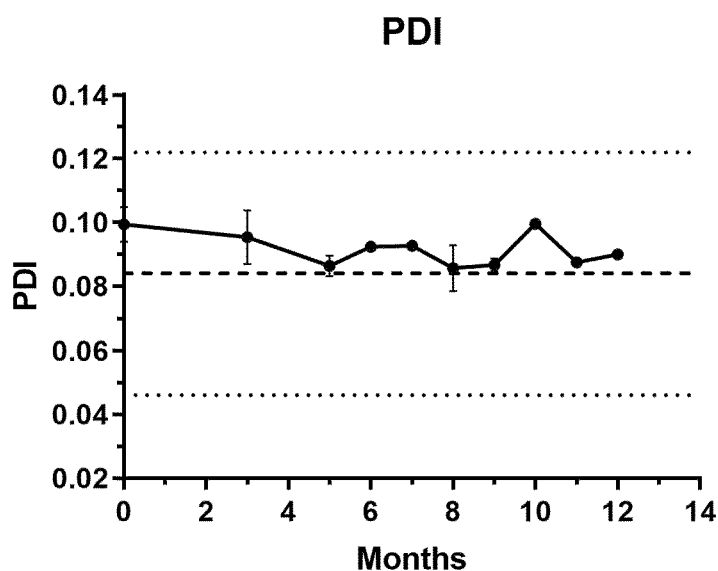

FIGS. 15a-b: size and polydispersity results of stability measurements over time (12 months) of liposomal doxorubicin formulation according to Expl 1.

EXAMPLE 1: PRODUCTION OF TLD-1

A 1,2-distearoyl-sn-glycero-3-phosphocholine and cholesterol were provided in a 60:40 weight ratio and dissolved in ethanol absolute >99.99%. The solution was hydrated in a 150 mM aqueous solution of ammonium sulfate in sterile water at 68° C. The solution was sonicated with amplitude of 60 μm for 24 hours to yield crude liposomes. PSPE-MPEG2000 aqueous solution was then added to the liposome suspension and heated to 65° C. for 30 minutes to yield PEGylated liposomes with the desired PEG-lipid amount of 5 mol %, corresponding to a PEG-lipid amount of 10 mol % in the outer one of be lipid bilayer. Doxorubicin HCl loading into liposomes was performed to achieve a DXR/total lipid weight ratio of 0.05 by remote load technique. Unloaded DXR was removed by gravity precipitation and filtration. The liposomal dispersion was washed by tangential flow filtration and buffer exchange was performed to achieve a dispersion of liposomes in 10 mM HEPES-buffered solution with 0.9 wt-% NaCl.

The liposomal doxorubicin obtained as described in this example may hereinafter be called "TLD", "TLD-1"o"Talidox".

Whenever free doxorubicin is applied as a comparative formulation, this may in the Examples and Figures be referred to as "Doxo", "DXR", "DX", "Doxorubicin".

COMPARATIVE EXAMPLE

Commercially available Caelyx® was purchased. For the cryo-TEM measurements, Caelyx® was diluted 10× in HEPES buffer (NaCl, pH 6.8).

EXAMPLE 2: SIZE MEASUREMENTS

Size measurement of the liposomes obtained by the above method was performed by cryo-TEM and DLS and the results compared to corresponding measurements of commercially available Caelyx® formulation.

Figure 1B:
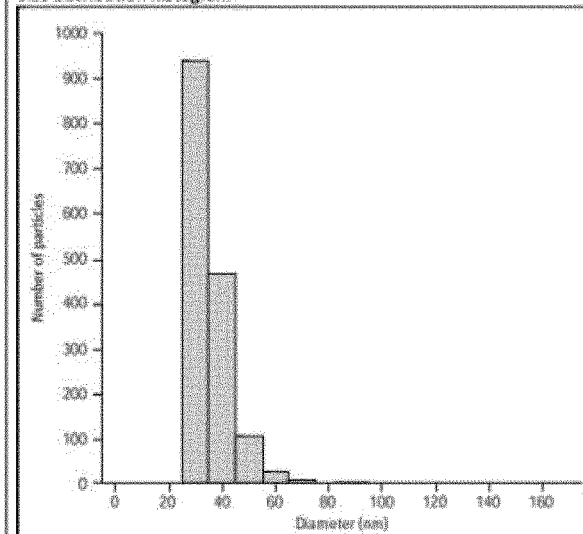
Figure 2B:
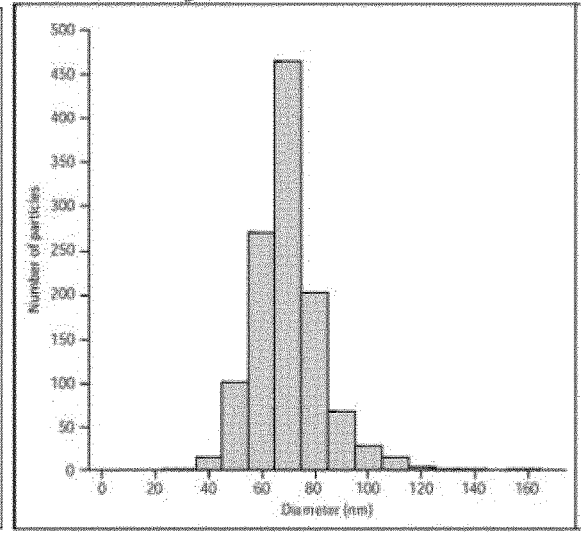

FIG. 1a shows a high magnification (80'000×) representative image of the formulation obtained according to Expl 1. FIG. 1b shows the measured size distribution histogram. FIG. 2a shows a high magnification (80'000×) representative image of the comparative Caelyx® formulation. FIG. 2b shows the measured size distribution histogram.

CryoTEM measurements were performed as follows: Liposomal samples according to Example 1 and comparative example were vitrified. The samples were prepared on-grid (Formvar and Carbon) with an acc. voltage of 200 kV. Images were acquired with a cryo-TEM JEOL JEM-2100F device and a TVIPS TemCam F415MP camera at 40,000× magnification. Particle identification and size determination were performed by semi-automated image processing using Vironova Analyzer Software, Vironova, Sweden. Briefly, a series of random images of the same magnification was imported. Only liposome particles located entirely within the boundaries of the image and with a distinct membrane were detected. The identified objects were analyzed for spherical diameter, circularity, unilamellarity. All images were batch-processed with identical thresholds and settings, accumulating over 5 to 18 images for each sample, corresponding to a number of analyzed particles of 1560 to 1178. Mean values have a standard deviation of approx. 10 nm.

FIG. 1b shows the size distribution of the liposomal formulation according to Expl 1. The No. of images analyzed was 5. The number of particles analyzed was 1560. The mean diameter was 35.61 nm and the standard deviation 7.42 nm. The smallest diameter measured was 24.81 nm, the largest diameter measured was 103.35 nm. Homogeneity Z-test gave a measure of the homogeneity of the sampling of 1.01, indicating that all images included in the analysis contained a population of particles with the same means size.

FIG. 2b shows the size distribution of the liposomal formulation according to the comparative example. The No. of images analysed was 18. The number of particles analysed was 1178. The mean diameter was 70.26 nm and the standard deviation 13.41 nm. The smallest diameter measured was 32.52 nm, the largest diameter measured was 159.09 nm. Homogeneity Z-test gave a measure of the homogeneity of the sampling of 3.15, indicating that not all images included in the analysis contained a population of particles with the same means size.

The liposomal formulations according to Expl 1 further showed a No. of broken particles <10%, and no particle aggregates nor clusters in the cryoTEM analysis.

FIG. 3 shows a size of liposomal formulations according to Expl. 1 and comparative example, measured by dynamic light scattering (DLS). Both samples were diluted 10-fold in PBS or MQ $H_2O$ and measured on a Zetasizer device by Malvern at 25° C. and 0° scattering angle. TLD-1 (according to Expl 1) had a mean diameter of 60.5 (±4.7 nm) nm and a polydispersity index of 0.084±0.038. Caelyx® had a mean diameter of 85.0 nm in DLS-measurements. It shall be noted that the values measured by dynamic light scattering are slightly higher than the values obtainable by cryoTEM imaging due to the PEGylated surface not being detectable by cryoTEM, while it is included in DLS as part of the hydrodynamic radius of liposomes.

EXAMPLE 3: CIRCULARITY MEASUREMENTS

Circularity of the liposomal formulations according to Expl 1 and comparative Expl was measured by Cryo-TEM. The results are presented in FIG. 4a for Expl 1 and in 4b for comparative Expl. Sample preparation and measurements were performed as described earlier.

For Expl 1, the mean circularity of the particles was 0.99 with a relative standard error of 0.03% and a mean standard deviation of 0.01. The $50^{th}$ percentile was measured 1.00, the $10^{th}$ percentile 0.98, the $5^{th}$ percentile 0.98, and the $2^{nd}$ percentile 0.96. Homogeneity Z-test gave a measure of the homogeneity of the sampling of 1.19, indicating that all images included in the analysis contained a population of particles with the same means size.

For the comparative example, the mean circularity of the particles was 0.99 with a relative standard error of 0.06% and a mean standard deviation of 0.02. The $50^{th}$ percentile was measured 1.00, the $10^{th}$ percentile 0.97, the $5^{th}$ percentile 0.95, and the $2^{nd}$ percentile 0.92. Homogeneity Z-test gave a measure of the homogeneity of the sampling of 6.10, indicating that not all images included in the analysis contained a population of particles with the same means size.

Commercially available Caelyx® hence shows a lower degree of circularity of the liposomes in formulation. For example, 10% of the liposomes in Caelyx® have a circularity of only 0.97 and lower.

The liposomal formulations according to Expl 1 further showed a filling rate (filling with doxorubicin) of at least 80% and a unilamellarity rate of 98% in the cryoTEM measurements.

EXAMPLE 4: CRYSTAL DIMENSIONS AND NUMBER OF FIBRES PER CRYSTAL

Dimensions of the liposomal formulations according to Expl 1 and comparative Expl were measured by Cryo-TEM. The results of the width measurements are presented in FIGS. 5a and 5b for Expl 1 and in 5c for the comparative Expl. The results of the length measurements are presented in FIGS. 6a and 6b for Expl 1 and in 6c for the comparative Example. Sample preparation and measurements were performed as described earlier. The crystal length and width were measured manually from a set of high magnification images obtained by Cryo-TEM.

For Expl 1, the mean crystal width was 9.57 nm with a standard deviation of 2.78 nm (No. of measurements: 140; 12 images analysed) and the mean crystal length was 27.36 nm with a standard deviation of 9.15 nm (No. of measurements: 289; 5 images analysed). For the comparative example, the mean crystal width was 17.45 nm with a standard deviation of 4.60 nm (No. of measurements: 60; 21 images analysed), and the mean crystal length was 47.77 nm with a standard deviation of 15.33 nm (No. of measurements: 105; 5 images analysed).

Amount of fibers per liposomes was determined from a set of high magnification images obtained by Cryo-TEM. The number of individual fibers (high density nodes) per liposome could be derived manually. Since the doxorubicin crystals have a helical conformation and the number of individual fibers per turn may vary, one measurement was taken per turn, in order to provide an accurate representation.

For Expl 1, the class ratios are displayed in FIG. 7a. For the comparative example, the class ratios are displayed in FIG. 7b. The x-Axis shows the class number (1 to 12), wherein the class number indicates the number of individual fibers in the doxorubicin crystal.

In Expl. 1, a number of 3 fibers per crystal was the most frequent conformation. No crystals with 1, 7 or more individual fibres were observed. The average distance between individual fibres for all doxorubicin crystals in the dataset was measured to 2.6 nm.

In comparative Expl., a number of 7 fibers per crystal was the most frequent conformation. No crystals with 1, 2, 3 and 12 or more individual fibres were observed. The average distance between individual fibres for all doxorubicin crystals in the dataset was measured to 2.7 nm.

Commercially available Caelyx® hence shows a lower degree of circularity of the liposomes in formulation. For example, 10% of the liposomes in Caelyx® have a circularity of only 0.97 and lower.

The liposomal formulations according to Expl 1 further showed a filling rate (filling with doxorubicin) of at least 80% and a unilamellarity rate of 98% in the cryoTEM measurements.

EXAMPLE 5: TUMOR ACCUMULATION IN MICE

A liposomal doxorubicin formulation according to Expl 1 ("TLD-1"), commercially available Caelyx® ("CAELYX") and free doxorubicin (Adriblastin; "free Doxorubicin") were administered to mice (athymic Nude-Foxn1$^{nu}$ mice) in an amount of 3.5 mg/kg. After 4 h or 16 h, the mice were sacrificed in order to detect the total doxorubicin amount using HPLC analysis.

FIG. 8 shows the doxorubicin accumulation in liver and tumor over time for three compared administered formulations. Bars represent mean and standard deviation (n=3).

TLD-1 accumulation was about 4× higher than accumulation of free doxorubicin in the tumour and twice as high as for CAELYX®. The serum half-life up to 16 hrs is comparable between CAELYX and TLD-1. Liver accumulation and clearance, however, is more efficient for TLD-1.

EXAMPLE 6: CYTOTOXICITY IN VITRO

In vitro cytotoxicity of TLD-1, CAELYX and free doxorubicin ("DX") was measured in A2780 cells seeded at 10'000 cells/ml in 96 wells plates (100 ml/well). 24 hrs after seeding, the cells were treated with different concentrations of doxorubicin formulations.

FIG. 9 shows the result of added concentrations of 10, 50, 100, 500, 1000, 5000 and 10'000 ng/ml to the cells. 72 hrs after treatment, MTS colorimetric assay components ((3-(4, 5-dimethylthiazol-2-yl)-5-(3-carboxymethoxyphenyl)-2-(4-sulfophenyl)-2H-tetrazolium) "MTS") were added for colouring viable cells. After another 3 hrs, absorbance was measured. As can be seen, absorbance of the samples treated with TLD-1 was clearly lower than absorbance of the samples treated with CAELYX for any applied concentration. Therefore, cytotoxicity of TLD-1 is higher and more similar to free doxorubicin.

FIGS. 10a to 10c show the result of added concentrations of 5, 50, 500, 5000, 25,000 and 50,000 ng/ml. Cells were treated in the presence of a luciferase substrate and luminescence of the viable cells measured over time (6, 24, 48, 73 hrs after treatment). As can be seen from the charts, luminescence of the samples treated with TLD-1 was clearly lower than luminescence of the samples treated with CAELYX after 48 hrs. The effect was even more pronounced after 72 hrs. Therefore, cytotoxicity of TLD-1 is higher and more similar to free doxorubicin.

Serum leakage studies: An experiment was performed to assess to which extent TLD-1 and Caelyx® release free doxorubicin into RPMI (cell medium)+/-10% FCS medium over time. Free doxorubicin in said medium was measured after 72 h incubation of TLD-1 and CAELYX, respectively, in the RPMI medium+/-10% FBS at 370 in a metal beads bath, protected from light. Free and liposomal doxorubicin were detected by HPLC size exclusion chromatography at 478 nm (hence avoiding background absorption from proteins). Liposomal doxorubicin is complexed in aggregates and thus appears later than the free doxorubicin peak. The latter was identified by comparison with values from a free DX (adriblastin) control sample. A comparative analysis of the area under the curve of the peaks (liposomal doxo vs free doxo) was performed. Experiments revealed that both TLD-1 and Caelyx remain stable when challenged at 37° for 72 h in the medium used in the in-vitro experiments. The percentage of free DX in the solution was below 4% for incubated TLD-1 and below 6% for incubated Caelyx®. In general, TLD-1 leakage was lower than leakage of Caelyx. This indicates that the enhanced effect seen in in-vitro cell toxicity assays is due to increased cellular uptake rather than by leaking free doxorubicin into the medium.

EXAMPLE 7: TUMOR GROWTH

In vivo effect on tumor growth was determined by administering placebo formulations, TLD-1 and CAELYX to mice and by measuring the effect on tumor size over time.

FIG. 11 shows the result of such testing. Empty liposomes, free doxorubicin, Caelyx® and TLD-1 were administered on a regular basis to mice (5 mice/formulation) with injected MDA-MB231 cell lines. Each arrow indicates injection of a dose of 3. 5 mg/kg body weight. The effect of TLD-1 (measured in tumor weight growth, μg) was clearly better than the effect of Caelyx® already 3 days after the start of the treatment and remained substantial over 26 days.

FIGS. 12a and 12b show the result of another similar test setup. PBS, free doxorubicin, Caelyx® and TLD-1 were administered on a regular basis to mice (5 mice/formulation) with injected A2780 cell lines. For FIG. 12a, a formulation similar to the one in Expl 1 was administered, however, unlike in Expl 1, sonication was only performed under such conditions as to reach mean liposomal diameter of 86.78 nm and a polydispersity index of 0.117 both measured by DLS. For FIG. 12b, a formulation according to Expl 1 was administered, liposomes having a mean diameter of 64.87 nm and a polydispersity index of 0.168, measured by DLS.

Each arrow indicates injection of a dose of 3.5 mg/kg body weight. While in the test presented in FIG. 12a, the effect on tumor growth of TLD-1 with a mean diameter outside of the specification (>70 nm) was found to be inferior compared to treatment with Caelyx®, the effect of TLD-1 according to the specification was clearly better than the effect of Caelyx already after 19 days after the start of the treatment and remained substantial over another 12 days (measured in tumor weight growth, µg).

FIG. 13 shows the result of another similar test setup. Saline, Caelyx® and TLD were administered on a regular basis to mice with implanted 4T1 tumor (5 mice/formulation). The effect of TLD-1 was clearly better than the effect of Caelyx 12 days after the start of the treatment (measured in tumor size growth, mm$^3$).

FIG. 14 shows the in-vivo survival study for mice treated with saline, Caelyx® or TLD-1 (according to Expl 1, 5 mice/formulation) respectively. 60% of mice treated with TLD-1 survived until day 30 and 40% of mice until day 34. In contrast, 100% of the mice of the group treated with Caelyx® had died already on day 26.

EXAMPLE 8: OTHER STUDIES

Other comparative studies for a liposomal doxorubicin formulation according to Expl 1 (TLD-1) and Caelyx® were performed. They included side-effect studies and efficacy studies in animal models. For Expl 1, it also included serum half-life and Area Under Curve (AUC) studies in humans, as well as side-effect studies.

Serum half-life studies have been performed in human serum: Caelyx has been documented to have a half-life of 74 h in human serum. Currently serum half-life of TLD-1 in human is estimated from 5 patients and is about 100 h. Moreover, the Area Under the Curve (AUC) of the serum half-life data of TLD-1 shows to be larger than for a corresponding dose of Caelyx®, which means that higher drug exposition for a given dose is achieved. Drug exposition of a patient treated with TLD-1 (30 mg/m2) is higher than drug exposition of a patient treated with Caelyx® (37 mg/m2) despite the difference in dose.

Adverse effects studies have been performed in rats. Skin toxicity and in particular PPE (e.g. hand-foot-syndrome) was assessed during toxicology studies conducted in rats. Skin toxicity and in particular PPE were not promoted by the administration of TLD-1, even at high concentration of 6 mg/kg (male and female data pooled together due to lack of statistically significant difference). Similarly, neutropenia was assessed during toxicology studies conducted in rats (by neutrophile count). Neutrophile count varied not significantly upon TLD-1 administration even at high concentrations of 6 mg/kg (male and female data pooled together due to lack of statistically significant difference).

EXAMPLE 9: STABILITY RESULTS

FIGS. 15a and 15b show the size and polydispersity stability of liposomal formulations according to the invention over time, measured by DLS. The liposomal formulations were obtained according to the method described above (Expl 1). The liposomal formulations were stored in HEPES buffered solution at a pH-value of 6.5 to 6.8 and a temperature of 4° C. The variation in size was not higher than ±1 nm over a 12-months period from manufacture. Variation in polydispersity index was not higher than ±0.01, measured by DLS.

EXAMPLE 10: CLINICAL TRIAL RESULTS

A clinical study is currently being conducted in which a liposomal doxorubicin formulation according to Expl 1 (TLD-1) has so far been used in twelve patients with advanced solid tumors (Swiss Group for Clinical Cancer Research; Trial number: SAKK 65/16). The trial was designed as an open-label, single arm, multicentre, first-in-human, phase-1 trial. The primary objective of this trial was to identify the maximum tolerated dose (MTD) and the recommended phase 2 dose (RP2D) for TLD-1 in patients with advanced solid tumors. Further objectives of this trial were to evaluate the safety, preliminary anti-tumor activity and pharmacokinetics of TLD-1.

The interim report of this study states that TLD-1 can be safely administered up to a dose of 45 mg/m$^2$ every 3 weeks in patients with advanced, pretreated solid tumors. This dose is higher compared to Caelyx®, where the MTD is 50 mg/m$^2$ every 4 weeks. Furthermore, the number and severity of undesired side effects of TLD-1 was lower than with Caelyx®. Specifically (TLD-1 vs. Caelyx®), no clinically significant nausea (<8.3% vs. 38.5%), vomiting (<8.3% vs. 24.3%), alopecia (0% vs. 13.4%), or cardiac toxicity were observed while myelosuppression was rare and of mild degree (8.3% vs. 25.6%). No unexpected toxicities were reported.

Without being limited to this, it is hypothesized that the fewer side effects observed with TLD-1 compared to conventional liposomal formulations of doxorubicin, including Caelyx®, are due to the comparatively small liposome size and the high degree of homogeneity of the doxorubicin-loaded liposomes administered to the patients, in particular due to their pronounced circularity, low polydispersity, and high degree of uniformity (length and width) of the doxorubicin crystal fibres in the liposomes.

The invention claimed is:

1. A liposomal doxorubicin formulation, wherein the lipid bilayer of the liposomes comprises at least
    phosphatidylcholine;
    cholesterol;
    a polyethyleneglycol-lipid conjugate;
    wherein
        the liposomes have a mean diameter between 30 and 70 nm, measured by dynamic light scattering and expressed as a Z-average; and/or
        the liposomes have a mean diameter between 20 and 50 nm, measured based on cryo-TEM acquired images;
    wherein the liposomes have a mean relative circularity of at least 0.99, measured by Cryo-TEM, and where the 10th percentile is at least 0.98;
    and wherein the circularity is calculated according to the formula:

$$\text{Circularity} = \sqrt{\frac{4 \times \pi \times \text{Area}}{\text{Perimeter}^2}}.$$

and wherein the liposomal doxorubicin formulation comprises intraliposomal ammonium sulfate.

2. The liposomal doxorubicin formulation according to claim 1, wherein the lipid bilayer consists essentially of synthetic phosphatidylcholine, of cholesterol and of DSPE-PEG.

3. The formulation according to claim 1, wherein the polyethyleneglycol-lipid conjugate is located essentially exclusively on the outer layer of the lipid bilayer.

4. The formulation according to claim 1, wherein the relative amount of polyethyleneglycol-lipid conjugate in the lipid bilayer is at least 2 mol. %.

5. The formulation according to claim 1, wherein the drug to total lipid weight ratio is from 0.01 to 0.10.

6. The liposomal doxorubicin formulation according to claim 1, wherein encapsulated doxorubicin crystals have at least one of a mean fibre width of 5 to 15 nm and a mean fibre length of 15 to 40 nm.

7. The formulation according to claim 1, wherein the liposomes are dispersed in HEPES buffered solution.

8. A method for producing a liposomal doxorubicin formulation, comprising the steps of:
  a) Providing phosphatidylcholine and cholesterol in an organic solvent;
  b) Adding an aqueous liquid,
  c) Enabling liposome formulation by sonication,
  d) Modifying liposomes by PEGylation,
  e) Loading doxorubicin into liposomes;
  Wherein step c) is carried out such that
    The liposomes have a mean diameter between 30 and 70 nm, measured by dynamic light scattering and expressed as a Z-average; and/or
    The liposomes have a mean diameter between 20 and 50 nm, measured based on cryo-TEM acquired images;
  Wherein the liposomes have a mean relative circularity of at least 0.99, measured by Cryo-TEM, and where the 10th percentile is at least 0.98; and wherein the circularity is calculated according to the formula:

$$\text{Circularity} = \sqrt{\frac{4 \times \pi \times \text{Area}}{\text{Perimeter}^2}}.$$

And wherein the liposomal doxorubicin formulation comprises intraliposomal ammonium sulfate.

9. The method according to claim 8, wherein the method does not contain any extrusion step or any thin film hydration step.

10. The method according to claim 8, wherein step f) is followed by a step
  g) sterilization by filtration.

11. Liposomal doxorubicin formulation according to claim 1, wherein the liposomal doxorubicin formulation has a polydispersity index ≤0.15, measured by DLS.

12. The method of treating a patient by administering an effective amount of the liposomal formulation according to claim 1 to the patient.

13. The method of treating a patient suffering from cancer by administering an effective amount of the liposomal formulation according to claim 1 to the patient.

14. The method of treating a patient suffering from solid tumors, metastatic breast cancer, advanced ovarian cancer, Kaposi's sarcoma and multiple myeloma, by administering an effective amount of the liposomal formulation according to claim 1 to the patient.

15. The method of treating a patient suffering from uterine leiomyosarcoma by administering an effective amount of the liposomal formulation according to claim 1 to the patient.

16. The method of treating a patient suffering from adnexal skin cancer by administering an effective amount of the liposomal formulation according to claim 1 to the patient.

17. The method according to claim 12, wherein the treatment comprises the intravenous administration of the formulation.

\* \* \* \* \*